United States Patent
Haynes et al.

(10) Patent No.: US 7,485,152 B2
(45) Date of Patent: Feb. 3, 2009

(54) PROSTHETIC LEG HAVING ELECTRONICALLY CONTROLLED PROSTHETIC KNEE WITH REGENERATIVE BRAKING FEATURE

(75) Inventors: Michael L. Haynes, Columbus, OH (US); Marc D. Taylor, Columbus, OH (US)

(73) Assignee: The Ohio Willow Wood Company, Mount Sterling, OH (US)

( * ) Notice: Subject to any disclaimer, the term of this patent is extended or adjusted under 35 U.S.C. 154(b) by 654 days.

(21) Appl. No.: 11/212,359

(22) Filed: Aug. 26, 2005

(65) Prior Publication Data
US 2007/0050044 A1 Mar. 1, 2007

(51) Int. Cl.
A61F 2/48 (2006.01)
(52) U.S. Cl. .......................... 623/24; 623/45
(58) Field of Classification Search ............. 623/24–27, 623/39–46
See application file for complete search history.

(56) References Cited

U.S. PATENT DOCUMENTS

| | | | |
|---|---|---|---|
| 4,072,800 A | 2/1978 | Gammer ...................... 429/97 |
| 4,310,932 A | 1/1982 | Näder et al. .................... 3/28 |
| 4,595,179 A | 6/1986 | Glabiszewski .............. 267/8 R |
| 4,685,926 A | 8/1987 | Haupt ......................... 623/43 |
| 4,685,927 A | 8/1987 | Haupt ......................... 623/44 |
| 4,795,474 A | 1/1989 | Horvath ....................... 623/27 |
| 4,876,944 A | 10/1989 | Wilson et al. ................. 91/35 |
| 5,062,856 A | 11/1991 | Sawamura et al. ............ 623/24 |
| 5,062,857 A | 11/1991 | Berringer et al. ............. 623/25 |
| 5,133,773 A | 7/1992 | Sawamura et al. ............ 623/24 |
| 5,133,774 A | 7/1992 | Sawamura et al. ............ 623/24 |
| 5,246,465 A | 9/1993 | Rincoe et al. ................. 623/39 |
| 5,248,570 A | 9/1993 | Meier ......................... 429/121 |
| 5,344,446 A | 9/1994 | Sawamura et al. ............ 623/24 |
| 5,357,279 A | 10/1994 | Nakamura et al. ........... 348/207 |
| 5,383,939 A | 1/1995 | James ......................... 623/24 |

(Continued)

FOREIGN PATENT DOCUMENTS

EP 0549855 A2 9/1992

(Continued)

OTHER PUBLICATIONS

Kato, I., et al. *Clinical Testing of an Above Knee Prosthesis with Myoelectric Control*, pp. 389-397.

(Continued)

*Primary Examiner*—Bruce E Snow
(74) *Attorney, Agent, or Firm*—Standley Law Group LLP

(57) ABSTRACT

A prosthetic leg having an electronically controlled regenerative prosthetic knee. In certain embodiments of the present invention the knee may be passive, whereby it is used only to generate electrical energy. In other embodiments, the knee may be active, whereby it can be used to assist with or completely control gait, as well as to generate electrical energy. The knee makes use of an actuator motor/generator to control gait and/or to generate electrical energy. An electronic control system is provided to control overall operation of the prosthetic leg, to distribute generated electrical energy, and to transfer excess electrical energy to one or more storage devices for later use. A prosthetic leg of the present invention having an active prosthetic knee may be especially helpful in assisting an amputee with activities that impart a high torque load to the knee joint.

158 Claims, 19 Drawing Sheets

U.S. PATENT DOCUMENTS

| | | | |
|---|---|---|---|
| 5,391,953 A | 2/1995 | van de Veen | 310/80 |
| 5,405,407 A | 4/1995 | Kodama et al. | 623/44 |
| 5,443,524 A | 8/1995 | Sawamura et al. | 623/24 |
| 5,545,232 A | 8/1996 | Van de Veen | 623/39 |
| 5,545,233 A | 8/1996 | Fitzlaff | 623/43 |
| 5,571,205 A | 11/1996 | James | 623/24 |
| D383,542 S | 9/1997 | Wellershaus et al. | D24/155 |
| 5,728,174 A | 3/1998 | Fitzlaff | 623/46 |
| D402,368 S | 12/1998 | Holzapfel | D24/155 |
| 5,888,212 A | 3/1999 | Petrofsky et al. | 623/24 |
| 5,888,213 A | 3/1999 | Sears et al. | 625/24 |
| 5,888,237 A | 3/1999 | Shiraishi et al. | 623/44 |
| 5,893,891 A | 4/1999 | Zahedi | 623/24 |
| 5,899,943 A | 5/1999 | Shiraishi et al. | 623/44 |
| 5,961,556 A | 10/1999 | Thorn | 623/27 |
| 6,086,616 A | 7/2000 | Okuda et al. | 623/44 |
| 6,102,354 A | 8/2000 | Thorn | 248/406.2 |
| 6,113,642 A | 9/2000 | Petrofsky et al. | 623/24 |
| D439,339 S | 3/2001 | Sawatzki | D24/155 |
| D446,304 S | 8/2001 | Sawatzki | D24/155 |
| 6,379,393 B1 | 4/2002 | Mavroidis et al. | 623/25 |
| 6,500,138 B1 | 12/2002 | Irby et al. | 602/26 |
| 6,517,585 B1 | 2/2003 | Zahedi et al. | 623/24 |
| 6,610,101 B2 | 8/2003 | Herr et al. | 623/24 |
| 6,645,252 B2 | 11/2003 | Asai et al. | |
| 6,719,806 B1 | 4/2004 | Zahedi et al. | 623/24 |
| 6,740,125 B2 | 5/2004 | Mosler | 623/45 |
| 6,755,870 B1 | 6/2004 | Biedermann et al. | 623/24 |
| 6,764,520 B2 | 7/2004 | Deffenbaugh et al. | 623/24 |
| 6,966,882 B2 | 11/2005 | Horst | |
| 2001/0029400 A1 | 10/2001 | Deffenbaugh et al. | 623/24 |
| 2002/0052663 A1 | 5/2002 | Herr et al. | 623/24 |
| 2003/0187517 A1 | 10/2003 | Mosler | 623/26 |
| 2004/0039454 A1 | 2/2004 | Herr | 623/39 |
| 2004/0049290 A1 | 3/2004 | Bedard | 623/24 |
| 2004/0059433 A1 | 3/2004 | Slemker et al. | 623/38 |
| 2004/0064195 A1 | 4/2004 | Herr | 623/24 |
| 2004/0088057 A1 | 5/2004 | Bedard | 623/25 |
| 2004/0111163 A1 | 6/2004 | Bedard et al. | 623/33 |
| 2004/0181289 A1 | 9/2004 | Bedard et al. | 623/24 |
| 2004/0186591 A1 | 9/2004 | Lang | 623/39 |
| 2006/0155385 A1* | 7/2006 | Martin | 623/24 |

FOREIGN PATENT DOCUMENTS

| | | |
|---|---|---|
| EP | 0549855 A3 | 9/1992 |
| EP | 0549855 B1 | 9/1992 |
| GB | 2216426 | 10/1989 |
| WO | WO 99/00075 | 1/1999 |
| WO | WO 99/44547 | 9/1999 |
| WO | WO00/27318 | 5/2000 |
| WO | WO01/54630 A1 | 8/2001 |
| WO | WO2004/017871 A2 | 3/2004 |
| WO | WO2004/017871 A3 | 3/2004 |
| WO | WO2004/017872 A1 | 3/2004 |
| WO | WO2004/092606 A2 | 10/2004 |

OTHER PUBLICATIONS

Tomovic, R., et al., *Adaptive Reflex Control of Assistive Systems*, Advances in External Control of Human Extremities IX, pp. 207-213.

Horn, G.W., *Electro-Control: am EMG-Controlled A/K Prosthesis*, Med. & Biol. Engng., vol. 10, pp. 61-73, Pergamon Press, Printed in Great Britain, 1972.

Flowers, W.C., et al., *An Electrohydraulic Knee-Torque Controller for a Prosthesis Simulator*, Transactions of the ASME, Journal of Biomechanical Engineering, pp. 3-8, Feb. 1977.

Grimes, D.L., et al., *Feasibility of an Active Control Scheme for Above Knee Prostheses*, Transactions of the ASME, Journal of Biomechanical Engineering, pp. 215-221, Nov. 1977.

Flowers, W., et al., *A New System for Providing Individualized, Multi-Mode, A/K Prosthesis*, pp. 513-520, ECHE, 1978.

Grimes, D.L., et al., *Multi-Mode Above-Knee Prosthesis Controller*, IFAC Control Aspects of Prosthetics and Orthotics, Ohio, USA, pp. 43-53, 1982.

Myers, D.R., et al., *An Active EMG-Controlled A/K Prosthesis*, Session 2: Man-Machine Mechanical and Information Interface, IFAC Control Aspects of Prosthetics and Orthotics, Ohio, USA, pp. 35-41, 1982.

Arežina, P., et al., *Development of a Control Program for the Active Above-Knee Prosthesis*, Proceedings of the Eighth International Symposium on ECHE, Dubrovnik, pp. 215-223, 1984.

Koganezawa, K., et al., *A Development of A/K Prosthesis Adaptable to Voluntary Walking Period*, Proceedings of the Eighth International Symposium on ECHE, pp. 343-355, Dubrovnik, 1984.

Hortensius, Peter, et al., *A Microcomputer-Based Prosthetic Limb Controller: Design And Implementation*, Annals of Biomedical Engineering, pp. 51-65, v15, n1, 1987.

Spear, T.C.L.M. et al., *Sensors In Prosthetic Systems For Computer Controlled Walking*, Proceedings of the Ninth Annual Conference of the IEEE Engineering in Medicine and Biology Society, pp. 1094-1095, v2, Conf. Date Nov. 13-16, 1987.

Chitore, D.S., et al., *Digital Electronic Controller for Above Knee Leg Prostheses*, Int. J. Electronics, vol. 64, No. 4, pp. 649-656, 1988.

Rovetta, Alberto, et al., *Biorobotics in a New Artificial Leg*, Proceedings IROS '90, IEEE International Workshop on Intelligent Robots and Systems, pp. 971-976, v2, Conference Jul. 3-6, 1990.

Pelisse, et al., *The use of a microprocessor for the partial assistance of a prosthesis for above knee amputees*, Journal of Microcomputer Applications, pp. 145-153, v13, n2, Apr. 1990.

Peeraer, L., et al., *Development of EMG-based mode and intent recognition algorithms for a computer-controlled above-knee prosthesis*, J. Biomed. Eng., pp. 178-182, v12, May 1990.

Popovic, Dejan, et al., *Control aspects of active above-knee prosthesis*, (accepted in revised form Dec. 10, 1989), Int. J. Man-Machine Studies, 35, pp. 751-767, 1991.

Jin, Dewin, et al., *Influence of Adjustable Frictional Moments on Gait Patterns of a Prosthetic Knee with Controllable Moment*, IEEE International Conference on Systems, Man and Cybernetics, Intelligent Systems for the 21st Century, pp. 509-512, v1, 1995.

Buckley, John G., et al., *Energy Cost of Walking: Comparison of "Intelligent Prosthesis" With Conventional Mechanism*, Arch. Physical Medical Rehabilitation, pp. 330-333, v78, Mar. 1997.

Lawrence, Tracie L., et al., *Wireless In-Shoe Force System*, Proceedings—19th International Conference—IEEE/EMBS, Chicago, IL, pp. 2238-2241, Oct. 30-Nov. 2, 1997.

Datta, D., et al., *Conventional versus microchip controlled pneumatic swing phase control for trans-femoral amputees: user's verdict*, Prosthetics and Orthotics International, pp. 129-135, v22, Aug. 1998.

Suga, T., et al., *Newly designed computer controlled knee-ankle-foot orthosis (Intelligent Orthosis)*, Prosthetics and Orthotics International, pp. 230-239, v22, Dec. 1998.

Yack, H. John., et al., *Kinetic Patterns During Stair Ascent in Patients with Transtibial Amputations Using Three Different Prosthesis*, JPO, p. 57, v11, n3 1999.

Heller, B.W., et al., *A pilot study comparing the cognitive demand of walking for transfermoral amputees using the Intelligent Prosthesis with that using conventionally damped knees*, Clinical Rehabilitation, pp. 518-522, v14, Oct. 2000.

Stinus, H., *Biomechanics And Evaluation Of The Microprocessor-Controlled C-Leg*, Zeitschrift fuer Orthopaedie und ihre Grenzgebiete, pp. 278-282, v138 n3, May-Jun. 2000.

Williamson, Richard, et al., *Gait Event Detection for FES Using Accelerometers and Supervised Machine Learning*, IEEE Transactions on Rehabilitation Engineering, vol. 8, No. 3, Sep. 2000.

Henkel, Stephanie., *Building A Smart Prosthetic Leg*, Sensors Magazine Online, pp. 32-33, v17, n12, Dec. 2000.

Skelly, Margaret M., et al., *Real-Time Gait Event Detection for Paraplegic FES Walking*, IEEE Transactions on Neural Systems and Rehabilitation Engineering, pp. 59-68, vol. 9, No. 1, Mar. 2001.

Pappas, Ion, et al., *A Reliable Gait Phase Detection System*, IEEE Transactions on Neural Systems and Rehabilitation Engineering, pp. 113-125, vol. 9, No. 2, Jun. 2001.

Rovetta, Alberto, et al., *Biorobotic Criteria in the Design of a New Limb Prosthesis*, Proceedings of the 10th International Conference on Advanced Robotics. ICAR 2001, The Fundamentals: From Present to Tomorrow, pp. 443-449, 2002.

Zlatnik, Daniel, et al., *Finite-State Control of a Trans-Femoral (TF) Prosthesis*, IEEE Transactions on Control Systems Technology, pp. 408-420, vol. 10, No. 3, May 2002.

Schmalz, Thomas, et al., *Energy expenditure and biomechanical characteristics of lower limb amputee gait: The influence of prosthetic alignment and different prosthetic components*, Gait and Posture, pp. 255-263, v16, Dec. 2002.

Nosaka, Toshiya, et al., *Development of a New Prosthetic Knee Joint for Trans-Femoral Amputees and Its Evaluation by Biomechanical Gait Analysis*, Nippon Kikai Gakkai Ronbunshu C, pp. 3053-3060, v68, n10, Oct. 2002.

Canina, Marita, et al., *Innovatory bio-robotic system for the accumulation of the energy of step in a limb prosthesis*, Proceedings for the RAAD'3, 12th International Workshop, Robotics in Alpe-Adria-Danube Region, Cassino, May 7-10, 2003.

Canina, Marita, et al., Innovative System for the Accumulation of Energy of the Step in a Limb Prosthesis, Proceedings of the 11th World Congress in Mechanism and Machine Science, China Machinery Press, Edited by Tian Huang, Aug. 18-21, 2005, Tianjin, China.

Cohen, J.Y., *Electroactive Polymers as Artificial Muscles—A Primer*, Polymers and Separations Research Laboratory (PolySep), Copyright 2003, Last update: Jan. 3, 2004.

* cited by examiner

PROSTHETIC LEG HAVING ELECTRONICALLY CONTROLLED PROSTHETIC KNEE WITH REGENERATIVE BRAKING FEATURE

BACKGROUND AND SUMMARY OF THE INVENTION

The present invention relates to a prosthetic limb having a regenerative and electronically controlled prosthetic joint. More specifically, the present invention is directed to a prosthetic leg having a regenerative and electronically controlled knee joint capable of converting mechanical energy, normally dissipated during the gait cycle, into electrical energy. The electrical energy may either be used as generated, or may be stored for later use. Stored electrical energy can be subsequently released as necessary to assist with an amputee's gait cycle or to provide power to various other electrical energy consuming devices associated with the amputee.

Lower limb amputations can be classified as one of two types: below knee (BK), or above knee (AK). A below knee amputation occurs along a line through the tibia and fibula of the lower leg; with the knee joint remaining intact. An above knee amputation, however, is a transfemoral amputation; meaning that the knee joint is also removed.

Constructing a prosthetic limb for an AK amputee is a more complicated process than constructing one for a BK amputee. A BK prosthesis is fitted to the amputee's residual leg, with the amputee's knee joint providing necessary bending during the gait cycle. However, as the natural knee joint has been removed from an AK amputee, an AK prosthesis must be constructed to simulate knee flexion and extension if the amputee's gait when using the prosthesis is to have any semblance of normality.

To this end, typical AK prosthetic legs have been constructed with a flexible (hinged) joint connecting a lower leg portion to an upper socket portion which, in turn, fits to the amputee's residual leg. Such a prosthetic leg allows the amputee to freely swing the lower leg portion forward during the extension portion of the gait cycle, and also allows for the lower leg portion to fold backward during the flexion portion of the gait cycle. Such simplistic artificial knee joints can be problematic, however. For example, failure to fully swing the lower leg portion forward during the extension portion of the gait cycle can result in instability, as the knee joint may unexpectedly and undesirably bend under the amputee's weight. In addition to these drawbacks, the vaulting motion and subsequent flexion of the knee joint relies solely on energy input from the amputee and the resulting momentum of the gait cycle. Such knee joint operation can be very difficult for the amputee to control—especially as energy and momentum build. Further, using a prosthetic limb with such a knee joint can require a significant expenditure of energy, which may be especially difficult for elderly or infirm amputees.

In an attempt to better control the gait cycle of an AK prosthetic leg, both basic and electronically controlled passive knee joints have been developed. These knees employ devices such as pneumatic and hydraulic cylinders, magnetic particle brakes, and other similar damping mechanisms, to damp energy generated during the gait cycle so that the prosthetic leg moves through a more controlled range of motion. These damping devices also offer resistance to bending of the knee joint, thereby providing additional stability. Such devices must be designed and/or adjusted based on an amputee's weight, gait pattern, and activity level, among other factors. In the case of an electronically controlled passive prosthetic knee, a software enabled microprocessor and one or more sensors are typically used to monitor the gait cycle of the amputee and adjust the damping device accordingly.

While AK prosthetic legs employing these passive prosthetic knee joints are an improvement over limbs using earlier free-swinging knee joints, such legs still rely solely on energy input from the amputee and the resulting momentum of the gait cycle for their operation. Electronic control systems associated with these passive prosthetic knee joints also require a power source, such as a battery, for their operation.

Most known AK prosthetic legs typically focus on optimizing two specific indices of the gait cycle. The first of these indices is generally referred to as "heel rise," and can be described as the angle to which the knee flexes after the toe leaves the floor. During active gait, and without the affect of some restraining force, the heel can rise so far as to prevent it from properly traveling forward later in the gait cycle. Typical AK prosthetic limbs attempt to limit heel rise to around 60 degrees in order to best mimic normal gait.

The other focus of many known AK prosthetic limbs is typically referred to as "terminal impact." As the leg travels forward, the lower (shin) portion thereof swings towards an extended position and can obtain relatively high angular speeds relative to the thigh portion. Terminal impact is, therefore, defined as the impact that the lower portion of the prosthetic leg imparts to the rest of the prosthetic frame when it reaches its full extension and stops—usually just before the foot contacts the ground. Dissipation of this energy can result in a hammering effect on the frame potion of the prosthetic leg that is both uncomfortable for the amputee, and potentially destructive to the prosthesis.

The need for a highly active AK prosthetic leg to limit heel rise and terminal impact requires significant energy consumption by the amputee. The faster an amputee walks, the faster the prosthetic leg must move and the more energy the amputee must impart to the prosthetic leg. Unfortunately, much of the energy that is imparted to the prosthetic leg is lost on the next half step, either at the end of heel rise, or at terminal impact.

Various devices and methods have been developed to dissipate this energy. The most common of these devices and methods are friction, pneumatic, hydraulic, or magneto-rheological braking systems that simply convert the dissipated energy to heat. The result of using such devices and methods is that the faster an amputee tries to walk, the more energy they waste in each step. In effect, the amputee is penalized by the prosthesis for higher levels of activity because the energy cost per step rises rapidly with speed. For this, and other reasons, gait tends to be relatively slow in all but the most healthy and motivated AK amputees.

The aforementioned AK prosthetic legs also suffer from other drawbacks. For example, it has been found that, due to the significant energy input required, only a select few AK amputees are able to ascend stairs in a leg over leg manner using a prosthetic leg having a passive knee joint. Simply put, due to the lack of the natural knee joint and corresponding muscles, most AK amputees lack the strength necessary to ascend stairs in a conventional manner using a prosthetic leg with a passive knee joint.

In an attempt to alleviate these and other problems associated with known passive prosthetic knee joints, active prosthetic knee joints have been proposed. However, up until now these active prosthetic knee joints have suffered from various deficiencies including, among other things, the lack of accurate control, the lack of an acceptable actuator for imparting energy to the amputee's gait cycle, and the inability to produce a sufficient power supply for proposed actuators that can also be easily transported. For example, there have been proposals for hydraulically or pneumatically powered active prosthetic knee joints. Such designs have several drawbacks including, for example, the likelihood of leaks in the actuator or supply lines to the actuator, the build up of heat from repeated movement of the actuator, and problems associated with producing an acceptably sized portable hydraulic or pneumatic pump to power the actuator. Noise levels associated with operation of a power supply for such an actuator are also problematic. It has been further proposed to construct an active prosthetic knee joint using an electric motor(s). However, an external power supply is also required to power such a prosthetic knee joint. Additionally, proposed power supplies have been bulky, and cannot be comfortably or easily transported by an amputee. In a similar manner to the suggested hydraulically or pneumatically powered prosthetic knee joint, the proposed electrically powered knee joints have also been overly noisy.

SUMMARY OF THE INVENTION

Many research projects have found, and many journal articles have reported, that the amount of energy consumed by amputees using lower limb prosthetic devices is higher, often much higher, than that used by non-amputees. Yet, as discussed above, the use of the vast majority of known AK prosthetic legs results in substantial amounts of mechanical energy output by the amputee being essentially wasted. Therefore, the present invention is designed to overcome these and many other deficiencies associated with previously proposed AK prosthetic legs.

During normal gait, the human knee has been shown to absorb more energy than it expends. This is true for both a natural and prosthetic knee joint. Consequently, a properly designed prosthetic knee could actually operate in a manner that results in a net generation of electrical power.

Therefore, it is possible to collect the energy that is available from the knee during terminal impact and heel rise, and to then use this energy to augment other portions of the gait cycle or to power some other device. It has been determined that much of the excess energy that can be potentially recovered by a prosthetic knee originates at a patient's hip. For this reason, one such example would be to absorb energy from the knee and transfer this energy to hip extension, thereby returning the energy to it's original source, and reducing the necessary energy expenditure of the patient.

Thus, at a minimum, a prosthetic leg of the present invention includes a knee joint and associated components that convert mechanical energy produced during an amputee's gait cycle into electrical energy. The electrical energy can be used as it is generated and/or can be stored in one or more electrical energy storage devices. Some or all of the stored electrical energy may be subsequently used to power an associated electronic control system and possibly other related and/or unrelated electrical energy-consuming devices. In certain embodiments, a prosthetic leg of the present invention inputs at least some of the generated electrical energy back into the gait cycle as needed to control gait and/or assist the amputee with particular activities, such as ascending stairs or steep slopes, for example.

Because it has been found that more energy is actually dissipated by the prosthetic knee during the gait cycle than must be input thereto (i.e., the net energy requirement is negative), no external power supply is required. Rather, excess energy can be stored in compact batteries, capacitors, or other preferably high energy density electrical energy storage devices located in the knee or another portion of the prosthetic leg. In this manner, there will be enough electrical energy generated and stored to power at least the components of the prosthetic leg's electronic control system.

Further, certain embodiments of a prosthetic leg of the present invention can actively assist the amputee with high torque-producing activities such as rising from the floor or a chair, or stair ascent, without the need for the amputee to carry an external power supply. This is possible, because it is not necessary to store energy for all of the tasks in which an amputee would be expected to engage. It is only necessary to store energy for the few tasks expected to require the largest energy expenditure. Because these tasks are generally less frequent, once completed the knee can be expected to be used in a mode where it will be recharging in preparation for the next high energy task. Significantly, the presence of a regenerative system dramatically reduces the size of the power storage devices necessary to power such a knee.

It may also be possible to power other electrical energy consuming devices. Such devices may be associated with the prosthetic leg or may be unrelated to the prosthetic leg, and may even include other prosthetic limbs, such as a prosthetic hand or arm, for example.

In certain embodiments of a regenerative prosthetic leg of the present invention, a generator alone, or an actuator/generator combination, is used in conjunction with a knee damping device. The knee damping device may be provided in various forms, such as a hydraulic or pneumatic cylinder, or a magneto-rheological fluid employing damping or braking device. For example, in one exemplary embodiment, such a damping device is used for gait control and to assist the amputee in descending stairs and/or slopes. In such an embodiment, an actuator/generator can be used primarily to generate electrical power, although it may also be possible for the actuator function of the actuator/generator to provide an amputee with minimal assistance in high torque-producing activities such as ascending stairs, or rising from the floor or out of a chair, for example. This design allows for the actuator/generator to be sized so as to generate only the energy necessary to power the controls for the leg. Such a design also allows for a reduction in the complexity of the controls and reduces the overall size of the actuator/generator, actuator control hardware, generator control hardware (if distinct), power supply, and power storage device(s).

In another embodiment of a prosthetic leg of the present invention, an active prosthetic knee joint includes a damping device that can be used for basic gait control and to provide some level of assistance to the amputee in descending stairs and/or slopes, or in other similar activities. In this embodiment, the damping device is set to a gross stiffness value based on some predetermined properties of the amputee's gait cycle or of some standard gait cycle. For example, the stiffness of the damping device may be obtained from a look-up table based on the amputee's walking pace or a typical walking pace. In this particular embodiment, an actuator/generator is used to generate electric power, as well as to supplement the functions of the damping device. For example, if the amputee's pace changes after the gross stiffness of the damping device is set, the actuator/generator may be used to maintain proper gait control instead of continually adjusting the damping device. Again, it may also be possible for the actuator function of the actuator/generator to provide an amputee with at least minimal assistance in high torque-producing activities such as ascending stairs, or rising from the floor or out of a chair, for example.

In yet another embodiment of a prosthetic leg of the present invention, an active prosthetic knee joint includes an actuator/generator for actively controlling gait and generating electrical power. In this embodiment, the actuator/generator is used to actively modify the gait and in so doing provides the patient with improved gait. However, in this embodiment, the actuator/generator is not intended to generate the high torque output necessary for tasks such as, for example, climbing or descending stairs. Hence, in this embodiment an additional damping device (such as the hydraulic cylinder or pneumatic cylinder) is also provided—but only to assist the amputee in descending stairs and/or slopes, or in other similar high torque-producing activities.

While not a primary intent of this embodiment of the present invention, it is possible that such a device would be capable of providing an amputee with minimal assistance in high torque-producing activities such as ascending stairs, or rising from the floor or out of a chair, for example. This assistance might be sufficient to enable highly active patients to accomplish some tasks that they would otherwise be unable to perform.

In an alternate embodiment of an active prosthetic knee of the present invention, an actuator/generator is used without an additional damping device. In this embodiment, the actuator/generator is used for general gait control, to generate electrical power, and to actively assist the amputee with high torque-producing activities such as ascending and descending stairs and/or slopes, or rising from the floor or out of a chair. It is contemplated that the actuator/generator may be coupled to another drive mechanism(s) to provide for proper knee movement. Alternatively, it may also be possible to couple the actuator/generator directly to a pin or shaft that forms the knee's pivot axis.

In embodiments of the prosthetic leg wherein the actuator/generator actively provides for or assists with gait control, the actuator/generator is able to operate as an actuator (i.e., in actuator mode), driving a mechanism that causes powered movement of the prosthetic knee joint. For example, when an amputee is rising from the floor or a chair, ascending stairs, or walking very quickly or very slowly, stored power may be drawn from the energy storage device(s) and provided to the actuator/generator so that the prosthetic knee can be caused to actively assist the amputee in moving the prosthetic leg. When an amputee is descending stairs, sitting down, or walking at a normal pace, for example, the actuator/generator may operate predominantly as a generator/brake (i.e., in generator mode), damping movement of the knee and converting dissipated mechanical energy into electrical energy for operation of the associated electronic control system and/or ancillary electrical energy-consuming devices.

Electrical energy in excess of that needed for immediate consumption can be stored in one or more electrical energy storage devices. This stored electrical energy may later be used to actively move the prosthetic knee using the actuator/generator in actuator mode, to power an electronic control system, or to operate one or more other electrical energy consuming devices used by the amputee. Therefore, electrical energy collected in the present invention may be used as it is generated, or it may be converted and stored for use during future activities of the amputee.

The present invention includes one or more devices in conjunction with an electronic control system that is responsible for controlling electrical energy generation, distribution, storage, and discharge. The electronic control system is also in communication with various sensors that allow it to monitor and control overall operation of the prosthetic leg. The electronic control system may employ a plurality and variety of such sensors in order to obtain the feedback necessary for automatic operation and adjustment of the prosthetic leg. One or more electrical energy storage devices are also typically provided for storing excess electrical energy generated during ambulation by the amputee.

Further, the present invention includes devices having a powered prosthetic knee joint that can actively assist an amputee with ambulation using electrical energy that has been generated by movement of the prosthetic leg. Consequently, certain embodiments of a prosthetic leg with an active prosthetic knee joint of the present invention can be used to assist an AK amputee in movement of an AK prosthetic leg without the need for an external power supply. These and other aspects of the present invention are more particularly described and/or will become better understood from the following detailed description and accompanying drawing figures.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein:

FIG. 5b is an enlarged view of a lower portion of the prosthetic leg and the knee joint of FIG. 5a;

FIG. 6b is an enlarged view of a lower portion of the prosthetic leg and the knee joint of FIG. 6a;

FIG. 7b is an enlarged view of a lower portion of the prosthetic leg and the knee joint of FIG. 7a;

FIG. 8b is an enlarged view of a lower portion of the prosthetic leg and the prosthetic knee of FIG. 8a;

FIG. 9b is a front cross-sectional view of the active prosthetic knee joint of FIG. 9a;

DETAILED DESCRIPTION OF THE EXEMPLARY EMBODIMENT(S)

As discussed above, it has been determined that for a large percentage of an individual's gait cycle, and particularly when descending stairs or slopes, the knee joint actually absorbs more energy than it must deliver. This is true for both a natural knee and for a prosthetic knee for use by an amputee. The absorbed energy results from the knee's required and repeated resistance to bending in the extension or flexion directions. This absorbed energy is typically dissipated as heat by known passive prosthetic knees. However, it is also possible to convert this absorbed mechanical energy into electrical energy, and to store the electrical energy for later use.

Figure 1:
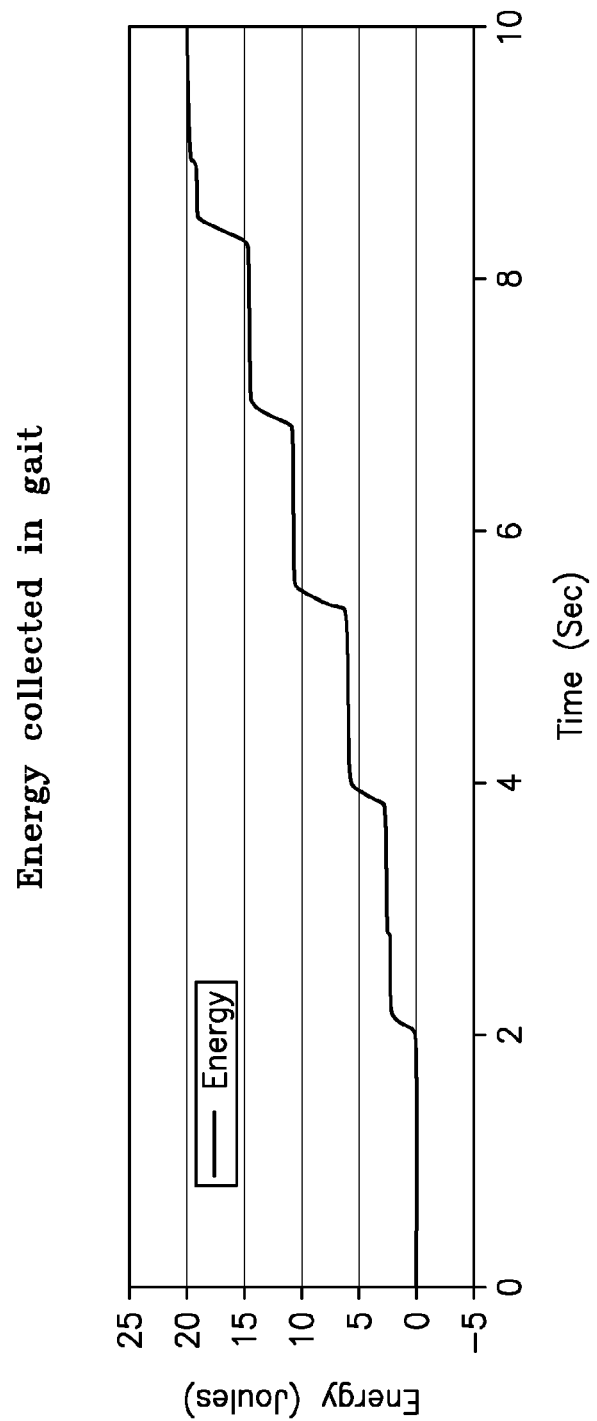
FIG. 1 is a graph depicting the energy generated by an electronically regulated knee joint of an AK prosthetic leg of the present invention while being used to limit heel rise and terminal impact during gait.

As can be observed by reference to the graph of FIG. 1, when using an AK prosthesis, energy must be absorbed from the knee during an amputee's gait cycle. The data shown in FIG. 1 was collected from an electronically regulated knee that was designed to simply mimic the function of current prosthetic knee designs. The data was collected while using the knee to limit heel rise and terminal impact associated with an AK prosthetic leg. However, no attempt was made to mimic normal gait. As shown in FIG. 1, each step of the gait cycle produced approximately 3-5 joules of energy.

Figure 2:
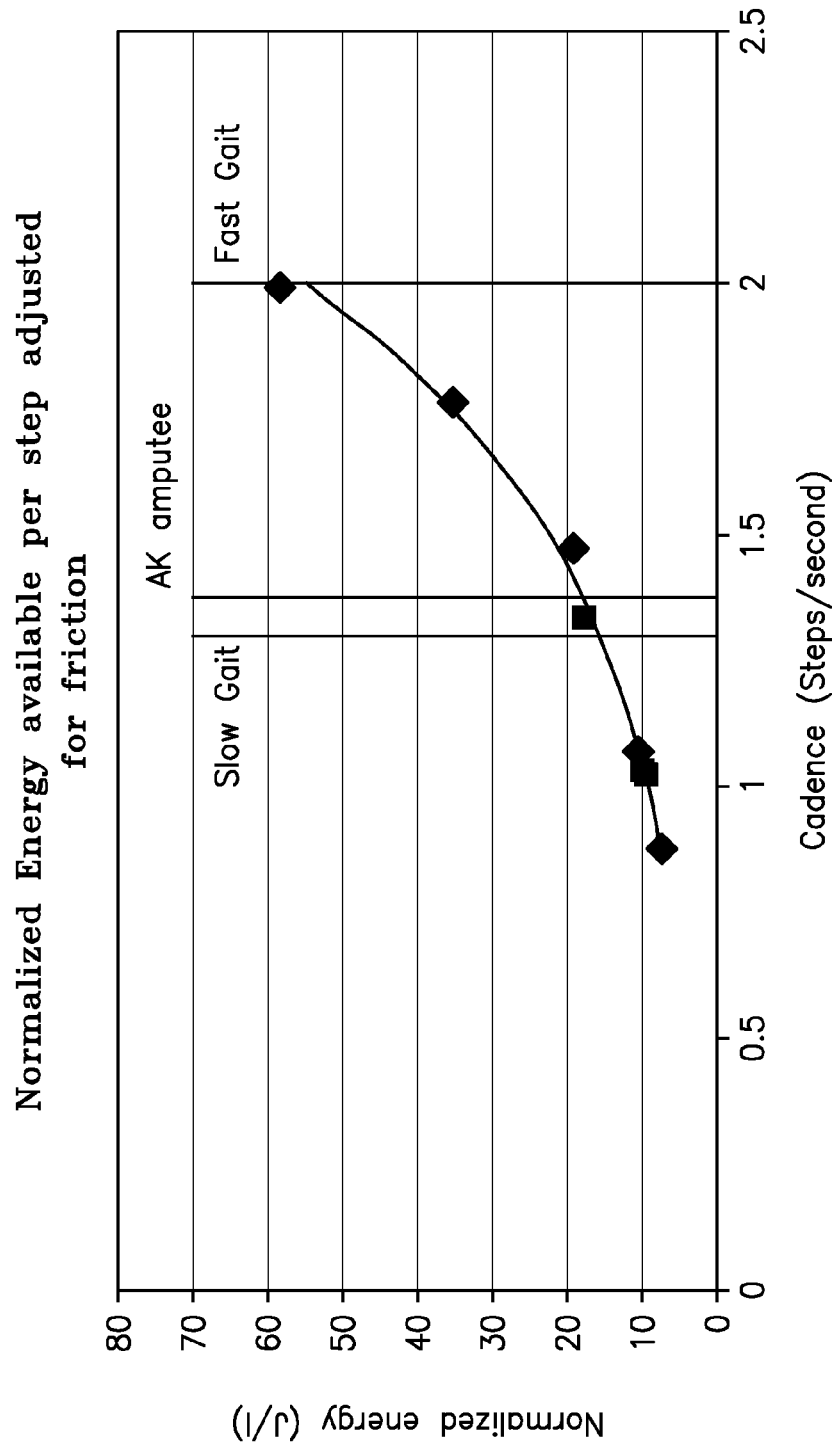
FIG. 2 is a graph illustrating approximately how much energy can be potentially produced in an electronically regulated prosthetic knee joint of an AK prosthetic leg of the present invention during a single walking step.

The graph of FIG. 2 illustrates the approximate amount of normalized energy available in a typical step of the gait cycle. It should be realized, however, that the amount of energy available form a single step is dependent on many parameters including, for example, gait speed, the size of the amputee, and the weight of the prosthetic leg. This data is found to follow a common trend once the generated energy is normalized by the moment of inertia (MOI) of the prosthesis about the knee joint.

As can be seen in FIG. 2, the energy generated increases in a non-linear manner as the speed at which the amputee walks increases. In this example, the MOI for a tall subject varied from about 0.1 to about 0.45 kgm$^2$, which approximately covers the range of expected prosthetic legs and feet currently on the market. The range of walking speeds shown in FIG. 2 covers even the extreme ranges of normal gait and includes the average selected walking speed for above knee (AK) prosthetic patient. The power generated in this particular example ranges from as little as about 3 watts to as high as about 58 watts, although the latter case represents a somewhat extreme walking speed at which a non-amputated subject would normally be expected to transition to running if allowed. At the lower end of normal gait, the data corresponds to an energy output of approximately 1 joule per step. Consequently, it is evident that a substantial and useable amount of energy is generated during the gait cycle, even at slow gait speeds.

In comparison to normal gait, stair ascent and stair descent have the potential to consume and generate, respectively, much more energy. However, published literature describes that BK amputees tend to climb stairs in a manner different than non-amputees. That is, they adopt a stair climbing method that transfers much of the work normally done by the knee to the hip, thereby reducing the amount of energy that would otherwise be consumed by manipulating the prosthetic limb. Additional research has revealed that a prosthesis with an active knee allows an AK amputee to adopt a similar stair-climbing strategy and to use substantially less energy than would otherwise be required. Adopting such a stair-climbing strategy seemed to be fairly automatic for subjects who were used to test active prosthetic knees according to the present invention, as attempting to minimize the load on the prosthesis appeared to be a natural reaction. Despite such adjustments, however, stair climbing was deemed comfortable by the test subjects.

Figure 3:
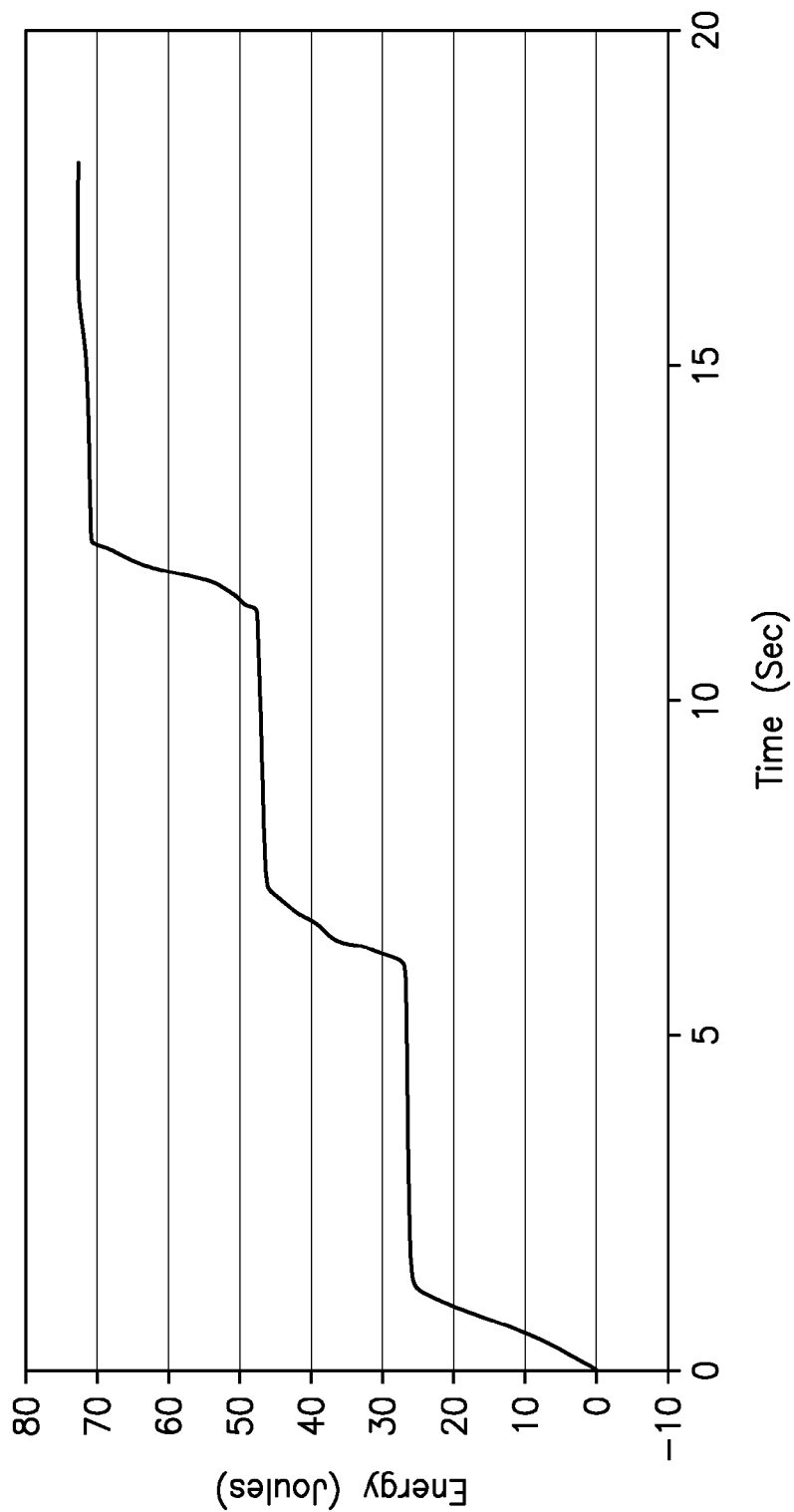
FIG. 3 is a graph showing the amount of energy consumed by one embodiment of an electronically regulated prosthetic knee joint of the AK prosthetic leg of the present invention while ascending stairs during a test.
Figure 4:
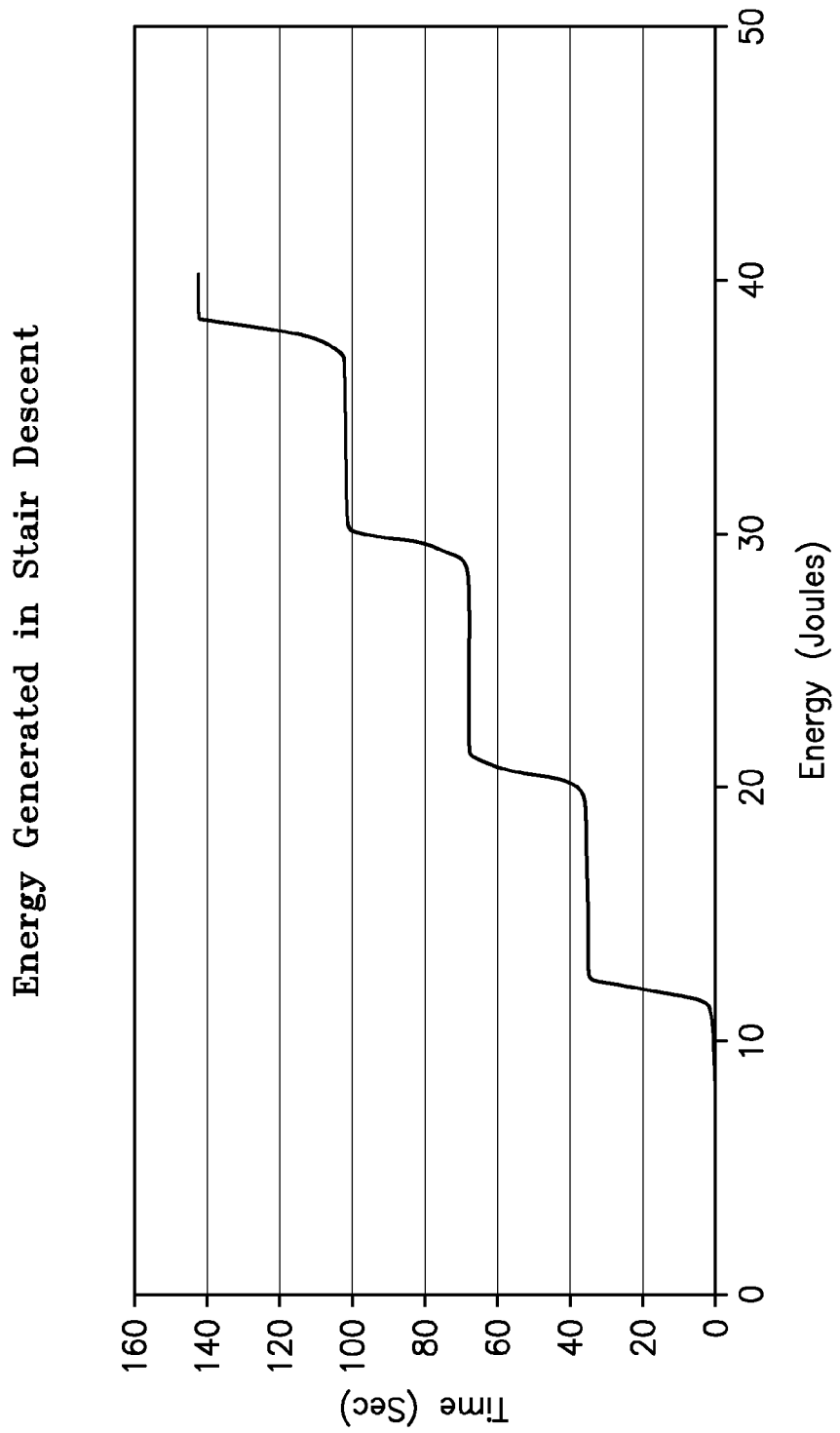
FIG. 4 is a graph showing the amount of energy generated in one embodiment of an electronically regulated prosthetic knee joint of an AK prosthetic leg of the present invention while descending stairs during a test.

The graph of FIG. 3 presents data collected as a test subject ascended three stairs during testing. As can be observed, energy consumption during this particular test ranged between about 20-25 joules per step. However, as illustrated in FIG. 4, approximately 25-40 joules of energy per step were generated during stair descent. This indicates that more energy is generated by resistance of the knee to bending during stair descent than is consumed by actuation of the prosthetic leg during stair ascent. Consequently, a positive amount of net energy is produced by ascending and subsequently descending a set of stairs. In other words, an amputee that climbs and then descends a flight of stairs using a prosthetic leg/knee of the present invention could actually experience a gain in stored energy.

Therefore, in comparison to a typical AK prosthetic leg/knee, which simply damps knee movement and dissipates absorbed mechanical energy as heat, a prosthetic leg of the present invention is provided with an electronically controlled knee joint having regenerative braking. Consequently, a prosthetic leg of the present invention is able to absorb otherwise dissipated mechanical energy, convert the otherwise dissipated mechanical energy into electrical energy, and use the generated electrical energy to power one or more electrical energy consuming devices used by the amputee. If desired, excess electrical energy may be saved in one or more compact electrical energy storage devices for later use. If provided, such electrical energy storage device(s) are preferably housed in or on the prosthetic knee or another portion of the prosthetic leg, thereby eliminating the need for an amputee to carry an external power supply. Because the knee joint also absorbs more energy during even typical ambulation than it must deliver, the electrical energy storage device(s) can be automatically charged via the electronic control system. Therefore, the need for an amputee to manually replace or recharge an electrical energy storage device(s) is also obviated.

In certain embodiments of a prosthetic leg of the present invention, gait control may be accomplished solely through use of a passive damping device in communication with an electronic control system. Such a prosthetic leg may include, for example, a hydraulic or pneumatic cylinder, or some form of a magneto-rheological fluid employing damping or braking mechanism. In these embodiments, an actuator/generator is used to convert dissipated mechanical energy into electrical energy for concurrent use by control electronics associated with the leg or by one or more related or unrelated electrical energy consuming devices associated with the amputee. Excess electrical energy is preferably stored. In such an embodiment the actuator/generator generally plays no significant role in gait control.

In other embodiments of the present invention, the prosthetic leg may actively assist an amputee in ambulation. Such a prosthetic leg may include a hydraulic or pneumatic cylinder, a magneto-rheological fluid employing damping or braking mechanism, or some other similar device that is able to damp large knee torques, in conjunction with an actuator/generator that operates in generator mode to convert dissipated mechanical energy into electrical energy, and in actuator mode to supply energy to the gait cycle when needed. In such embodiments, the actuator/generator may modulate the amputee's gait to varying degrees while the damping device provides the resistance to bending necessary to complete tasks beyond the resistive capacity of the actuator/generator. In one embodiment, the actuator/generator might be used to provide fine control of gait while the damping device is set to a gross stiffness value. In another embodiment, the actuator/generator might be sized to allow full control of regenerative gait, while the damping device is used only for supplemental damping during tasks producing high knee joint torques, such as stair descent or stumble recovery, for example. In either of these embodiments, the prosthetic leg is also able to actively assist an amputee in ascending stairs or slopes, or in other activities that would require a large energy input by the amputee.

In alternate embodiments of an active prosthetic leg of the present invention, an actuator/generator may be used without an additional damping device. In these embodiments, the actuator/generator provides for the conversion and dissipation of mechanical energy into electrical energy, for general gait control, and for the damping necessary to resist stair or slope descent or other activities that result in high-torque loads at the knee joint in either the flexion or extension direction. In such embodiments, the prosthetic leg is also able to actively assist an amputee in ascending stairs or slopes, or in performing other activities that require a large energy input by the amputee.

As mentioned above, and as will be better understood from the following descriptions of the prosthetic legs/knees of FIGS. 6-10, the included actuator/generator can operate in two different modes. In a first (active or actuator) mode, the actuator/generator can be used to actively assist the amputee with ambulation or other tasks. For example, if the onboard electronic control system determines that a gait adjustment is necessary, electric power may be supplied to the actuator/generator to actively control knee movement and, subsequently, to adjust the amputee's gait. The actuator/generator may also operate in actuator mode to actively assist an amputee with activities such as, climbing stairs or ascending slopes, and/or with rising from the ground, the floor, a chair, or a multitude of other non-erect positions. More generally, in this mode of operation the actuator/generator can assist with activities that produce torques about the knee joint in either the flexion or extension direction, and in the direction of motion of the knee joint.

In a second mode of operation, the included actuator/generator operates as a generator. Thus, in contrast to the above-described actuator mode of operation, wherein electric power is supplied to the actuator/generator—the actuator/generator produces electric power when in generator mode. As discussed earlier, normal movement of the prosthetic leg during ambulation of an amputee dissipates more energy than is required to produce the movement. Due to the large amount of kinetic energy stored in a lower portion of the leg relative to an upper portion of the leg, it has been discovered that the amount of energy dissipated is between approximately 3.5-4.0 times greater than the amount of energy that must be supplied to the gait cycle by the amputee. The dissipated energy results from the need to decelerate the rotational speed of the knee joint as the leg swings through a complete gait cycle. The actuator/generator is used to affect this deceleration, or resistance to motion, by installing it to the prosthetic leg in a manner that results in its forced rotation when flexion or extension torques are applied to the knee joint. Consequently, the actuator/generator produces electric power that can be concurrently used to power various electrical energy consuming devices or stored for later use. The actuator/generator may be installed to the prosthetic leg as part of a drive assembly or in some other manner.

Figure 5A:
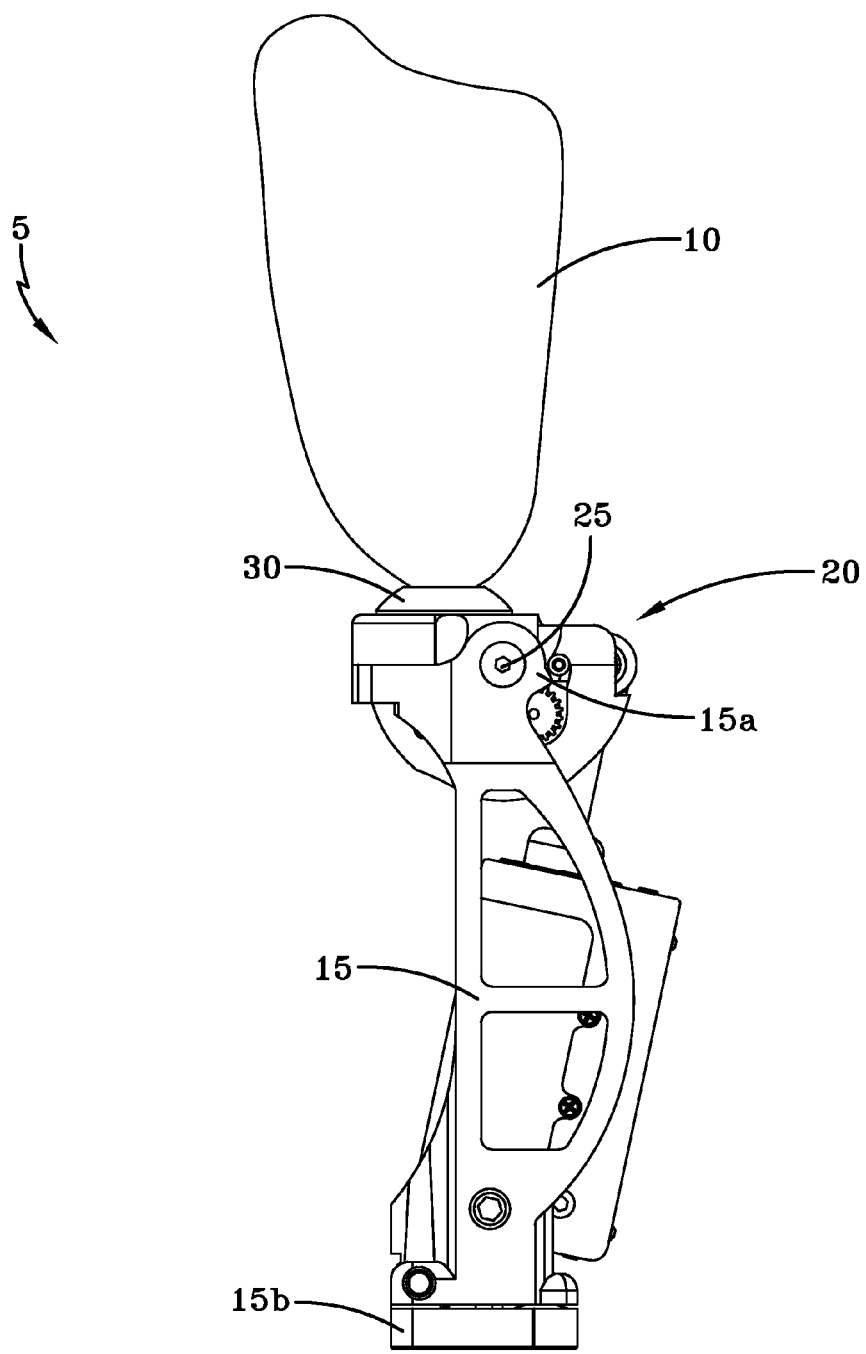
FIG. 5a is a side view depicting one embodiment of a prosthetic leg of the present invention, which includes a passive prosthetic knee joint in which an actuator/generator assembly functions only in a generator mode.
Figure 5B:
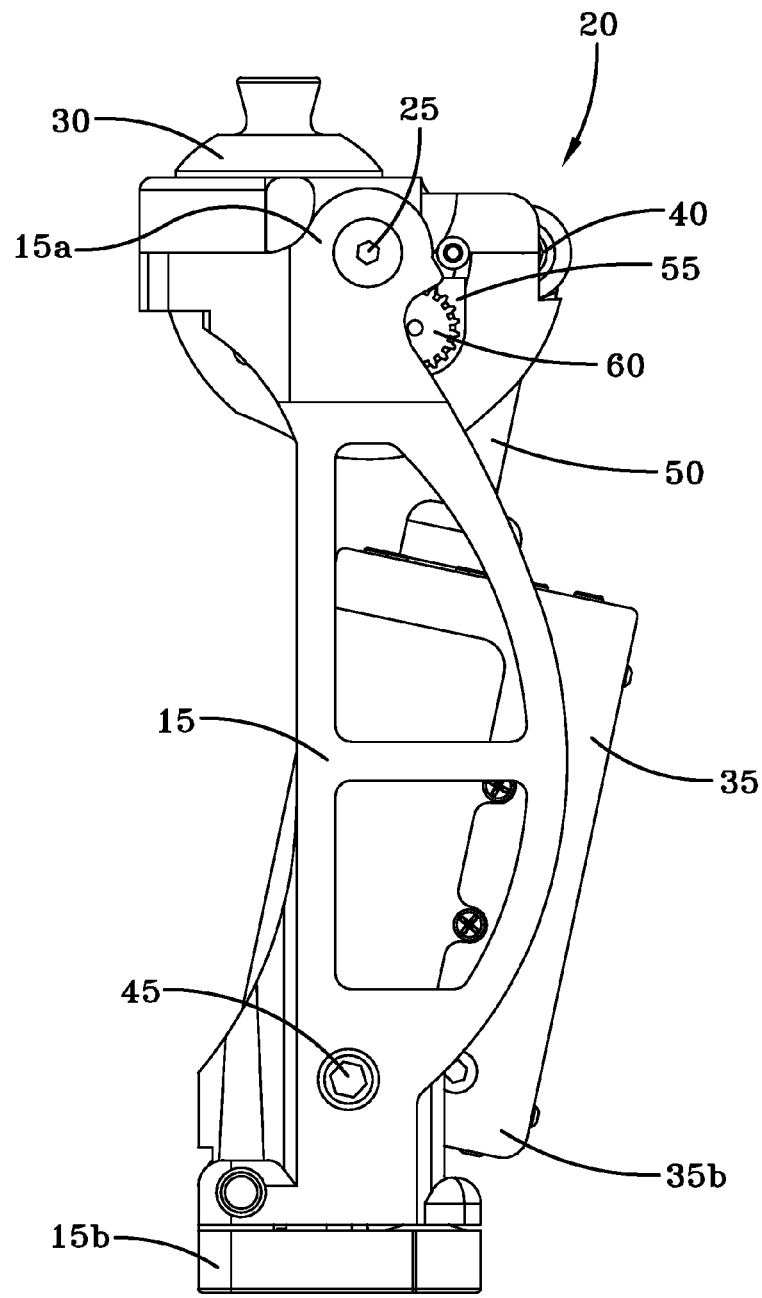

One exemplary embodiment of an above knee (AK) prosthetic leg 5 of the present invention having a regenerative but passive prosthetic knee 20 can be observed in FIGS. 5a-5b. The prosthetic leg 5 can be seen to have an upper portion consisting of a prosthetic socket 10 to be worn over an amputee's residual limb. It should be pointed out, however, that the attachment point of any prosthetic leg of the present invention to an amputee is not limited to a socket, but could also be effectuated by an implanted anchor, or other means that would be understood by one skilled in the art. A lower portion of the prosthetic leg 5 includes a frame 15. A distal end 15b of the frame 15 may be adapted for pivotal connection to a shin piece, a prosthetic foot, or a prosthetic ankle (not shown). A proximal end 15a of the frame 15 is adapted for pivotal connection to the prosthetic knee 20, such as by means of a knee joint pin 25 or similar connecting element that also serves as the rotational axis of the knee joint. This pivotal connection may be a simple single axis joint, however, one skilled in the art would understand that the connection could also be a device such as a four-bar linkage or some other polycentric joint. The knee 20 is also adapted for connection to the prosthetic socket 10, such as by means of the pyramid connector 30 shown.

In this embodiment, the prosthetic knee 20 includes a damping device for gait control and to assist the amputee in descending stairs and/or slopes. A hydraulic cylinder 35 is depicted as the damping device in FIGS. 5a-5b, although it should be realized that other adjustable damping devices, such as, for purposes of illustration and not limitation, a pneumatic cylinder or a magneto-rheologic based damper, could also be used. A particularly well-suited hydraulic cylinder for use in this embodiment of the prosthetic knee 5 is described in detail in U.S. patent application Ser. No. 11/112,155, entitled Electronically Controlled Damping Cylinder Having Dual Control Valves And Central Fluid Path and filed on Apr. 22, 2005, which is hereby incorporated by reference herein.

A distal end 35b of the hydraulic cylinder 35 is attached to the frame 15 via a lower pivotal connection 45. The cylinder rod 50 of the hydraulic cylinder 35 is attached to the prosthetic knee 20 via an upper pivotal connection 40. Rotation of the knee joint 20 about the knee joint pin 25 will, therefore, cause an extension or retraction of the hydraulic cylinder rod 50. Consequently, by adjusting the damping properties of the hydraulic cylinder 35, variable resistance to knee joint rotation can be provided.

The prosthetic knee 20 also includes a actuator/generator 55. In this particular embodiment, the actuator/generator 55 is used primarily to generate electric power. In this embodiment, the actuator/generator 55 resides within the prosthetic knee 20 and is provided with an input gear 60 that meshes with a corresponding fixed gear (not shown) located on the knee joint pin 25. As such, rotation of the prosthetic knee 20 during ambulation of the amputee causes a corresponding rotation of the input gear 60 and driving of the actuator/generator 55. Electrical energy produced by mechanically driving the actuator/generator 55 can be used to power electrical energy consuming devices associated with the prosthetic leg 5, such as an onboard electronic control system and/or the electronics associated with the actuating valve(s) of the hydraulic cylinder 35. Electrical energy produced by driving the actuator/generator 55 can also be used to power electrical energy consuming devices not associated with the prosthetic leg 5, such as, for example, other prosthetic limbs, remote sensors, implants (e.g., pacemakers or urinary assist devices), or personal electronic devices such as cell phones, personal digital assistants (PDA's), portable music players and the like. Excess electrical energy may be stored in one or more batteries, capacitors, or other suitable electrical energy storage devices that can be located in or on the prosthetic leg 5. This stored electrical energy can then be subsequently used as needed to power the electronic control system and/or one or more other electrical energy consuming devices as described above.

Depending on the power output capacity of the actuator/generator 55 used, it may also be possible for the prosthetic leg 5 to actively assist the amputee with high torque-producing activities such as stair ascent, or rising from the floor or a chair, for example. In such a case, the actuator/generator 55 would draw electrical energy from the electrical energy storage device(s) to cause a rotation of the input gear 60. Rotation of the input gear 60 by the actuator/generator 55 will cause a rotation of the prosthetic knee 20 about the knee joint pin 25 due to meshing of the input gear 60 and the fixed gear. Because the knee joint 20 is in a fixed relationship with respect to the prosthetic socket 10 and the residual leg, rotation of the knee joint causes a flexion or extension of the prosthetic leg 5.

Figure 6A:
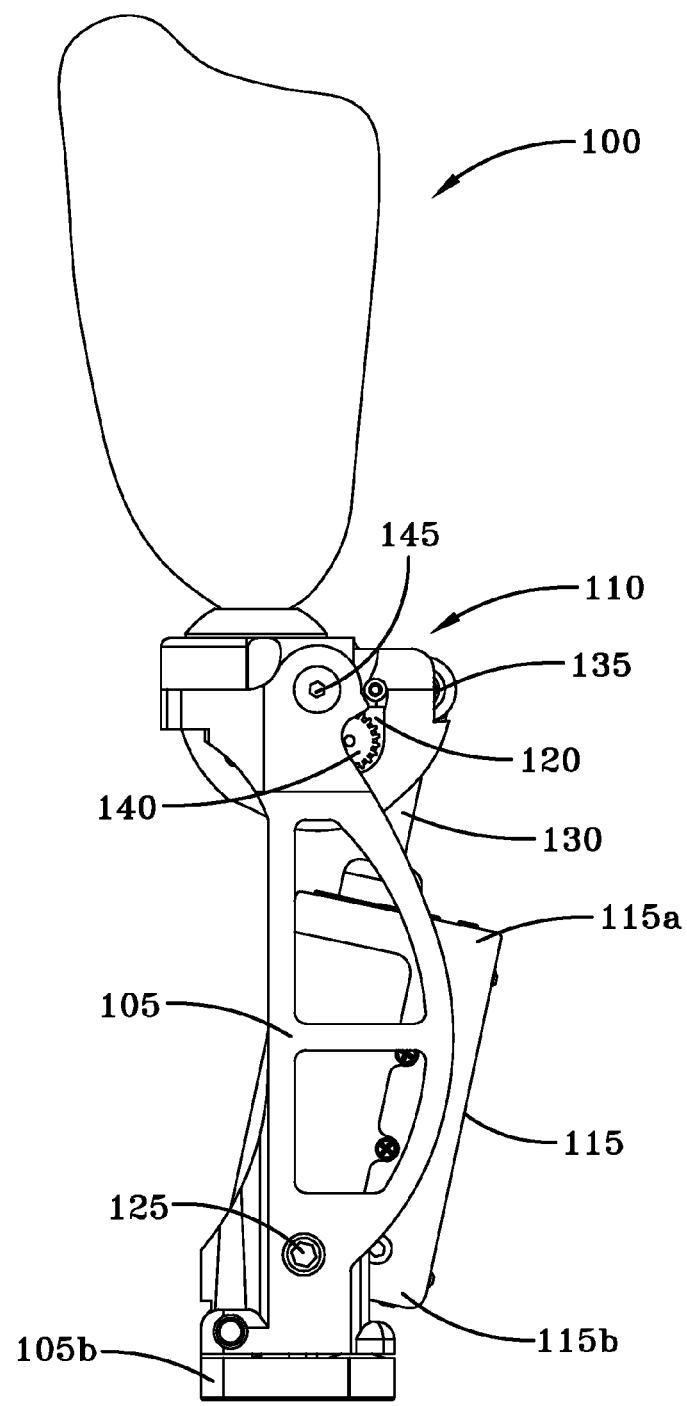
FIG. 6a is a side view depicting one embodiment of a prosthetic leg of the present invention having an active prosthetic knee joint with regenerative braking, and wherein sufficient actuator/generator capacity is provided to augment operation of a damping device and to provide for fine control of gait.
Figure 6B:
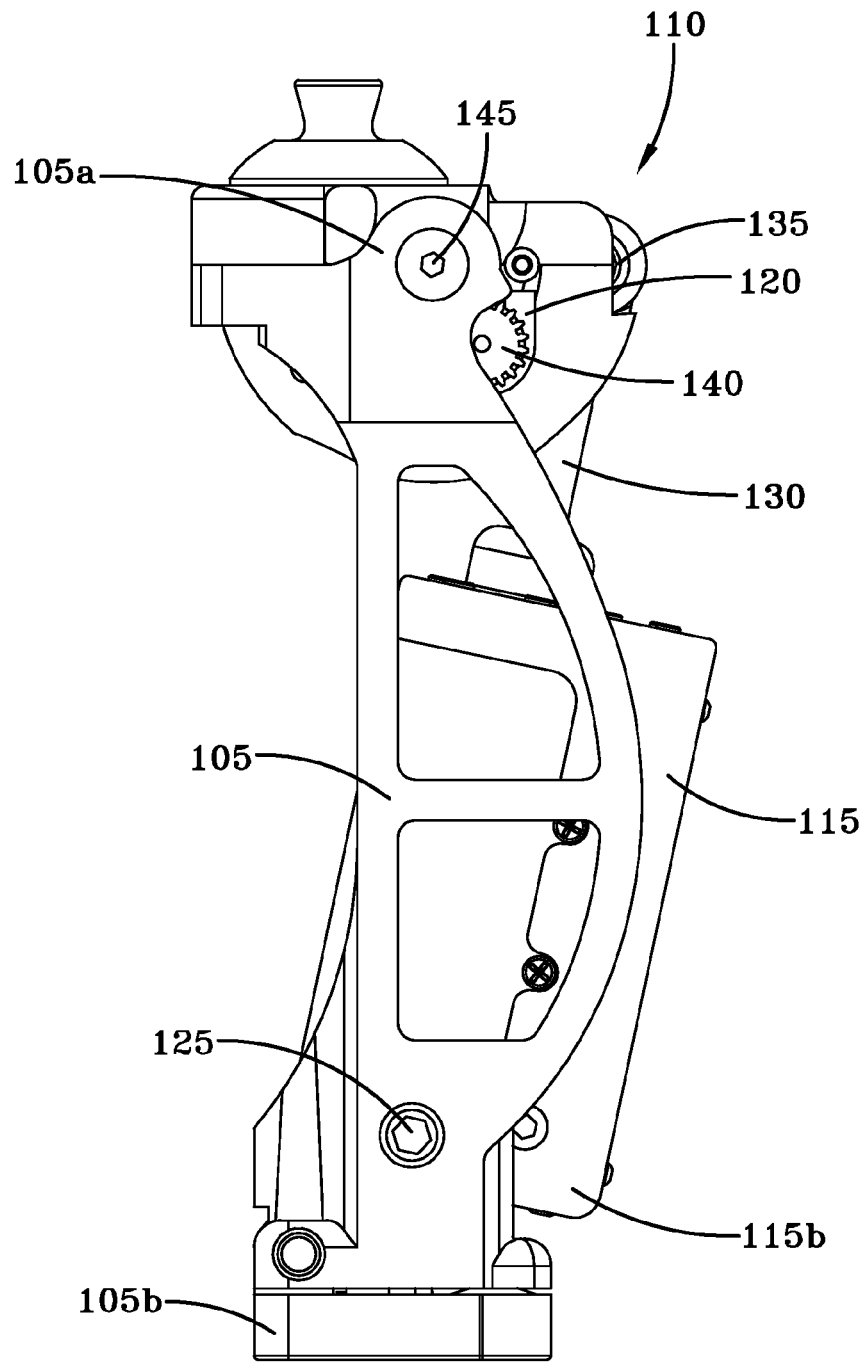

Another exemplary embodiment of an above knee (AK) prosthetic leg 100 of the present invention having a regenerative and active prosthetic knee 110 can be observed in FIGS. 6a-6b. In this embodiment, a damping device 115 is again used for primary gait control and to assist the amputee in descending stairs and/or slopes. A hydraulic cylinder is again employed as the damping device 115, although it should be realized that other adjustable damping devices, such as those previously mentioned, may also be used. In this embodiment, the damping device 115 is preferably set to a gross stiffness value based on some predetermined properties of the amputee's actual gait cycle. For example, the stiffness of the damping device 115 may be obtained from a look-up table based on the amputee's average walking pace and, optionally, based on a variety of additional factors such as the amputee's weight. Alternatively, the gross stiffness value may be based on some calculated or measured standard gait cycle that may or may not be adjusted to account for particular characteristics of the amputee. In any event, the gross stiffness value is ideally chosen so that the gait cycle can be adequately regulated by making only minor adjustments to the stiffness (resistance) produced by the actuator/generator.

In this particular embodiment, an actuator/generator 120 is used to generate electrical power, as well as to supplement the control function of the damping device 115. For example, if the amputee's pace changes after the gross stiffness of the damping device 115 has been set, the actuator/generator 120 may be used in actuator or generator mode as required to maintain proper control of prosthetic knee (instead of continually adjusting the damping device). It may also be possible for the actuator function of the actuator/generator 120 to provide an amputee with minimal assistance in performing activities that impart a significant torque load to the knee joint, such as, for example, ascending stairs, or rising from the floor or out of a chair.

As can be seen, the prosthetic knee 110 and a prosthetic leg 100 employing the prosthetic knee, may look similar to those shown in FIGS. 5a and 5b. However, it is also possible for the prosthetic knee 110 and/or prosthetic leg 100 to have a different construction. For example, as would be understood by one skilled in the art, embodiments of the prosthetic knee may have a construction similar to that shown in FIGS. 7a and 7b, or an entirely different design.

In the embodiment of the present invention depicted in FIGS. 6a and 6b, a distal end 115b of the damping device 115 is attached to a frame 105 via a lower pivotal connection 125. A cylinder rod portion 130 of the damping device 115 is attached to the prosthetic knee 110 via an upper pivotal connection 135. Rotation of the knee joint 110 about its rotational axis 145 will, therefore, cause an extension or retraction of the cylinder rod 130. Consequently, by adjusting the damping properties of the damping device 115, variable resistance to knee joint rotation can be provided.

The actuator/generator 120 of this embodiment resides in the prosthetic knee assembly 110, and is provided with an input/output gear 140 that meshes with a corresponding fixed gear (not shown) located on the knee joint pin 135. As such, forced rotation of the prosthetic knee 110 during ambulation of the amputee causes a corresponding rotation of the input/output gear 140 and driving of the actuator/generator 120. Electrical energy produced by using the actuator/generator 120 in generator mode can be used to concurrently power electrical energy consuming devices associated with the prosthetic leg, such as the electronic control system or one or more other related or unrelated devices associated with the amputee. Such additional electrical energy consuming devices may include those discussed above, or other compatible devices not specifically named herein. Excess electrical energy may be stored in one or more electrical energy storage devices for later use. This stored electrical energy can then be subsequently used as needed to power the electronic control system and/or one or more other electrical energy consuming devices as described above.

When a gait adjustment is necessary, or bending resistance of the damping device 115 (at the gross stiffness setting) needs to be supplemented, such as may be necessary when an amputee descends stairs or a steep slope, for example, the actuator/generator 120 may be operated in actuator mode to adjust the control/operation of prosthetic knee 110. The electrical energy used to power the actuator/generator 120 may be used as it is generated, or may be drawn from the electrical energy storage device(s) where it was previously stored as a result of driving the actuator/generator in generator mode during ambulation of the amputee.

Figure 7A:
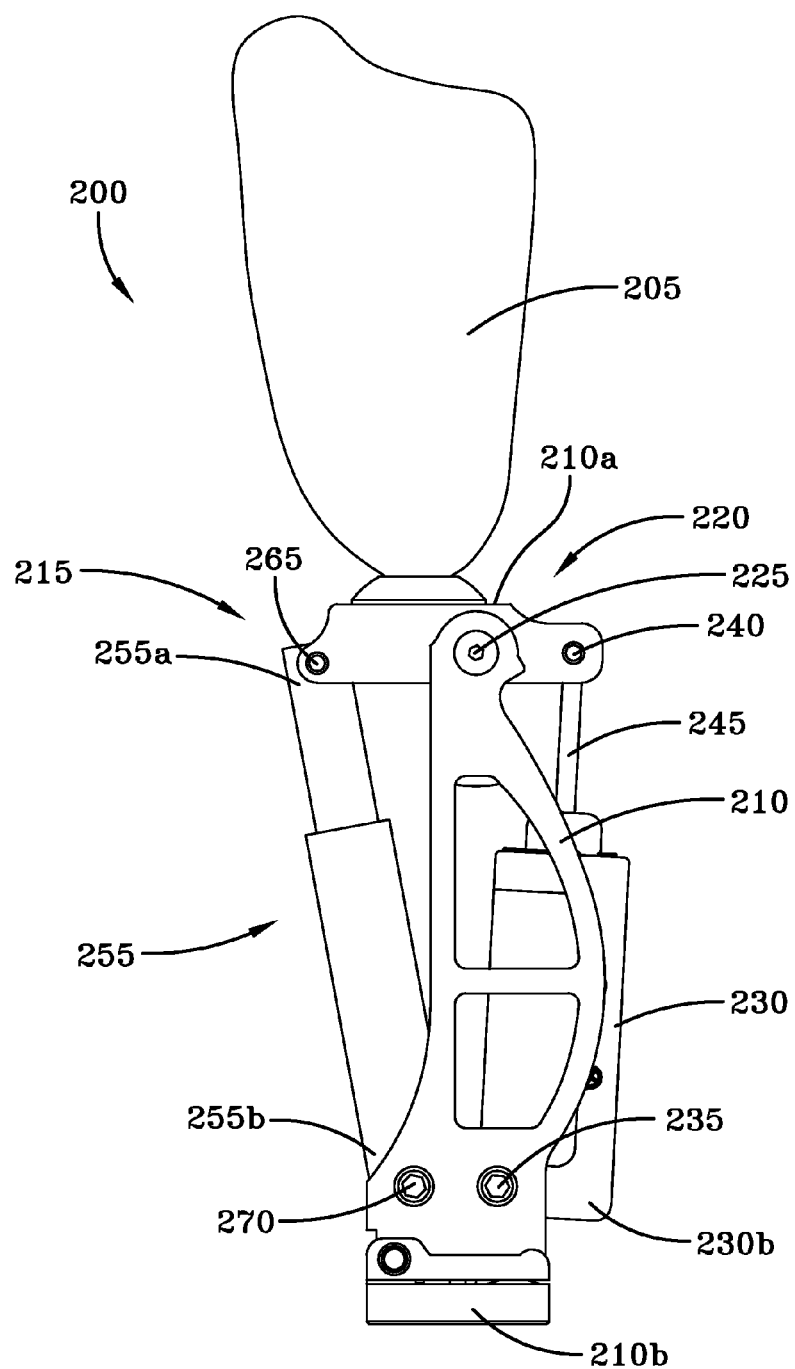
FIG. 7a is a side view depicting another embodiment of a prosthetic leg of the present invention having an active prosthetic knee joint with regenerative braking, and wherein an actuator/generator provides for primary gait control that is augmented by an auxiliary damping.
Figure 7B:
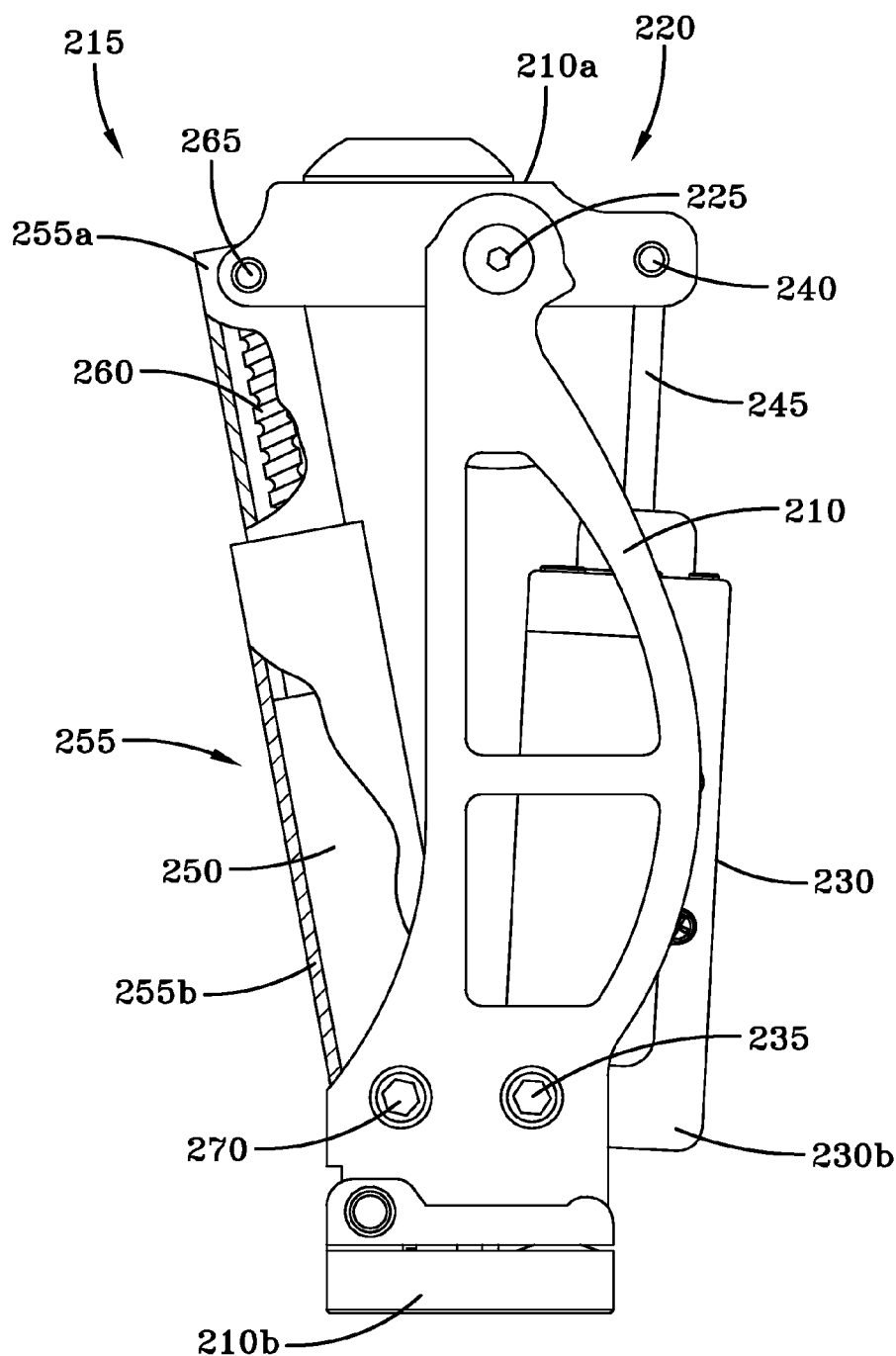

Yet another exemplary embodiment of an above knee (AK) prosthetic leg 200 of the present invention having a regenerative and active prosthetic knee 215 can be observed in FIGS. 7a-7b. In this embodiment, a actuator/generator 250 is used both for primary gait control and for generating electric power. A supplementary damping device 230 is used to further assist the amputee when the knee joint 220 is subjected to high torque loads in either the flexion or extension direction, such as commonly occurs when descending stairs and/or slopes, for example.

The regenerative and active prosthetic knee 215 is again included in an AK prosthetic leg 200 having a prosthetic socket 205. A lower portion of the prosthetic leg 200 includes a frame 210, which can be observed in greater detail in FIG. 7b.

A distal end 210b of the frame 210 may again be adapted for pivotal connection to a prosthetic foot or a prosthetic ankle (not shown), while the proximal end 210a of the frame is adapted for pivotal connection to the knee joint assembly 220, such as by means of a knee joint pin 225 or similar element. The knee joint assembly 220 is further adapted for connection to the prosthetic socket 205.

In this embodiment, the supplementary damping device 230 of FIGS. 7a and 7b is comprised of a damping cylinder, although it should be realized that other adjustable damping devices, such as those previously mentioned, may also be used. Because the supplementary damping device 230 is used only to offer resistance to bending during significant strenuous activities, such as stair or steep slope descent, the supplementary damping device may be smaller and/or less complicated in design than the hydraulic cylinder 35 shown in FIGS. 5a-5b and/or 6a-6b. A distal end 230b of the supplementary damping device 230 is attached to the frame 210 via a lower pivotal connection 235. A cylinder rod portion 245 of the supplementary damping device 230 is attached to the knee joint assembly 220 via an upper pivotal connection 240. Rotation of the knee joint assembly 220 about its rotational axis 225 will again, therefore, cause an extension or retraction of the cylinder rod 245. Consequently, by adjusting its compressive damping properties, the supplementary damping device 230 can be used to assist in resisting the significant torque loads that will typically be imparted to the prosthetic knee 215 during stair descent and similar other activities requiring high bending resistance.

The prosthetic leg 200 also includes an actuator/generator 250. In this particular embodiment, the actuator/generator 250 is used not only to generate electric power, but also to control gait. The actuator/generator 250 of the particular design shown resides between the knee joint assembly 220 and the frame 210 in an orientation similar to that of the supplementary damping device 230. More particularly, the actuator/generator 250 forms a portion of a drive assembly 255 that also includes a ball screw 260. The ball screw 260 is coupled to the actuator/generator 250. Depending on the particular actuator/generator used, a speed reducer may either be located between the output of the actuator/generator 250 and the input of the ball screw 260 or may be integral to the actuator/generator. A proximal end 255a of the drive assembly 255 is preferably attached to the knee joint assembly 220 via an upper pivotal connection 265, while a distal end 255b of the drive assembly is preferably attached to the frame 210 via a lower pivotal connection 270. In other versions of this embodiment, the actuator generator may be provided in a form identical or similar to that depicted in FIGS. 5a-5b, 6a-6b, or 9a-9b, or as some other non-illustrated design.

When gait adjustment is necessary, such as during walking by the amputee, electrical energy is supplied to the actuator/generator 250 under the command of an electronic control system. The resulting rotation of the actuator/generator 250 causes a rotation of the ball screw 260. Depending on the direction of rotation, the prosthetic leg 205 is subsequently adjusted toward a bent or straightened position. The amount, speed, duration, frequency, and other aspects of the adjustment(s) are determined and implemented by the electronic control system.

In this particular embodiment of the prosthetic leg 205, the repeated and forced rotation of the knee joint that normally occurs during the amputee's gait cycle results in the forced rotation of the ball screw 260 and the actuator/generator 250 connected thereto. Forced rotation of the actuator/generator 250 while in generator mode produces electrical energy that can be used to concurrently power the electronic control system or one or more other electrical energy consuming devices used by the amputee. Such additional electrical energy consuming devices may include those discussed above, or other compatible devices not specifically named herein. Excess electrical energy may be captured by regeneration circuitry of the electronic control system and stored in one or more electrical energy storage devices. This stored electrical energy can then be subsequently used as needed to power the electronic control system and/or one or more other electrical energy consuming devices as described above.

An even larger amount of electrical energy can be generated when an amputee descends stairs or a slope, for example, as an increased torque is applied to the prosthetic knee 215 and correspondingly transferred to the drive assembly 255. The stored electrical energy can subsequently be withdrawn from the electrical energy storage device(s) as needed to power the electronic control system, to operate the actuator/generator 250 in actuator mode when a gait adjustment is needed, and/or to power one or more other electrical energy consuming devices used by the amputee.

Figure 8A:
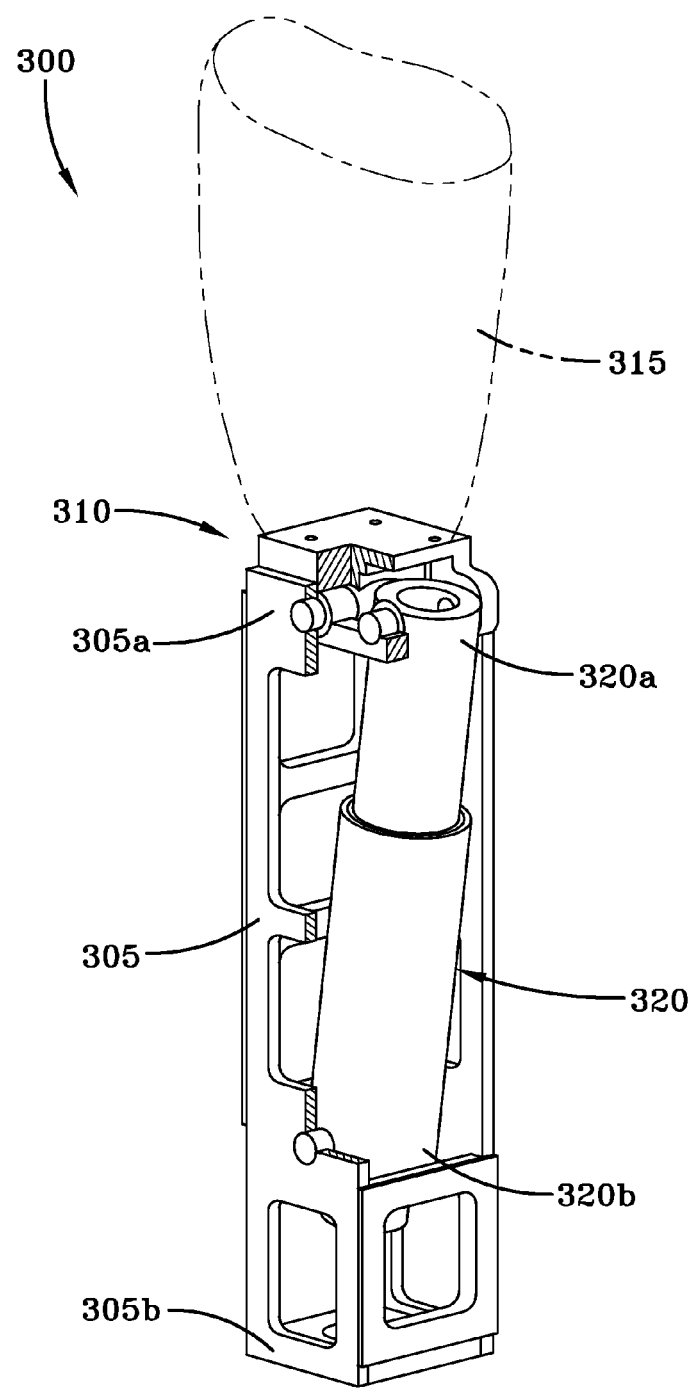
FIG. 8a is a side view depicting yet another embodiment of a prosthetic leg of the present invention having an active prosthetic knee joint with regenerative braking, wherein all regulation and control of gait is provided by an actuator/generator.
Figure 8B:
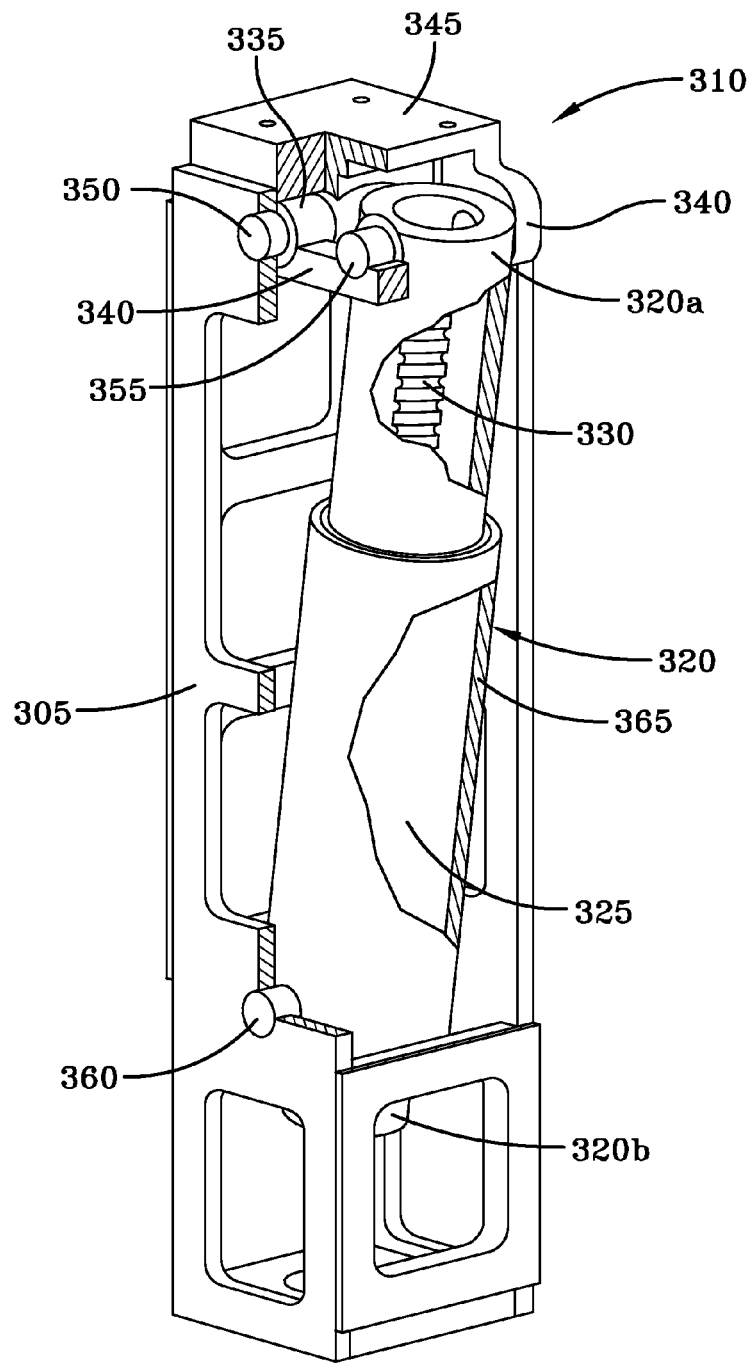

An alternate embodiment of an above knee (AK) prosthetic leg 300 of the present invention having a regenerative and active prosthetic knee 310 is shown in FIGS. 8a-8b. This particular embodiment of the prosthetic leg 300 employs a drive assembly 320 having an actuator/generator 325 coupled to a ball screw 330 to provide for overall gait control, and to actively assist the amputee with stair/slope ascent and other strenuous activities such as rising from the floor/ground or from a chair, for example. Unlike the previously shown and described prosthetic knee embodiments, this embodiment of the prosthetic leg 300 does not make use of an additional (supplementary) damping device.

A frame 305 is provided to act as the lower portion of the prosthetic leg 300. A proximal end 305a of the frame 300 is adapted for pivotal connection to a prosthetic knee assembly 310, while a distal end 305b of the frame may be adapted for (preferably pivotal) connection to a prosthetic ankle or prosthetic foot (not shown). The prosthetic knee assembly 310 is adapted for connection to a prosthetic socket 315. Connection of the frame 305 to a prosthetic ankle or foot, or connection of the prosthetic knee assembly 310 to a prosthetic socket 315, may be facilitated by one of the appropriate assemblies illustrated in FIGS. 5-7, for example. The frame 305 is also adapted to pivotally retain a distal end 320b of the drive assembly 320.

The prosthetic knee assembly 310 shown in this particular embodiment of the prosthetic leg 300 consists essentially of a mechanical knee joint 310 having a body portion 335 adapted for pivotal connection to the frame 305, a lever arm 340 portion adapted for pivotal connection to a proximal end 320a of the drive assembly 320, an upper portion 345 for attachment directly to the prosthetic socket 305 or to a prosthetic socket connector, and ancillary connecting hardware.

The knee assembly 310 may be pivotally coupled to the frame 305 by means of a hinge pin 350, a polycentric linkage, or a similar element, which also defines the axis of rotation for the prosthetic knee. Similarly, the lever arm 340 can be pivotally coupled to the proximal end 320a of the drive assembly 320 by means of a connecting pin 355 or similar element. A distal end 320b of the drive assembly 320 is similarly connected to the frame 305 via a lower pivotal connection 360. Roller bearings or other rotation-enhancing devices may be used along with the associated connecting means to facilitate rotation of any of the pivotally connected components.

The actuator/generator 325 of the particular design shown resides within a housing 365 of the drive assembly 320, which can be observed in greater detail in FIG. 8b. The drive assembly 320 extends upward from its connection point with the frame 305 to the lever arm 340 portion of the knee joint 310. The actuator/generator 325 is again coupled to a ball screw 330.

When active torques are necessary, such as during walking by the amputee, electrical energy is supplied under the command of an electronic control system to the actuator/generator 325 operating in actuator mode. The resulting rotation of the actuator/generator 325 causes a rotation of the ball screw 330, and a subsequent extension or retraction of the overall drive assembly (housing). Depending on the direction of rotation of the actuator/generator 325 and the resulting movement of the drive assembly 320, the prosthetic leg 300 is subsequently adjusted toward a bent or straightened position. The amount, speed, duration, frequency, and other aspects of the adjustment(s) are determined and implemented by the electronic control system.

In this particular embodiment of the prosthetic leg 300, the repeated and forced rotation of the knee joint 310 that inherently occurs during the amputee's gait cycle results in the forced rotation of the ball screw 330 and the actuator/generator 325 connected thereto. Forced rotation of the actuator/generator 325 while in generator mode produces electrical energy that can be captured by regeneration circuitry of the electronic control system and used to concurrently power an electronic control system or other electrical energy consuming devices used by the amputee. Such additional electrical energy consuming devices may include those discussed above, or other compatible devices not specifically named herein. Excess electrical energy may be captured by the regeneration circuitry and stored in one or more electrical energy storage devices. This stored electrical energy can then be subsequently used as needed to power the electronic control system and/or one or more other electrical energy consuming devices as described above.

An even larger amount of electrical energy can be generated when an amputee descends stairs or a slope, as an increased torque is applied to the knee joint 310 and correspondingly transferred to the drive assembly 320. The stored electrical energy can subsequently be withdrawn from the electrical energy storage device(s) as needed to power the electronic control system, other electrical energy consuming devices used by or associated with the amputee, and/or to power the actuator/generator 325 in actuator mode when a gait adjustment is needed.

Figure 9A:
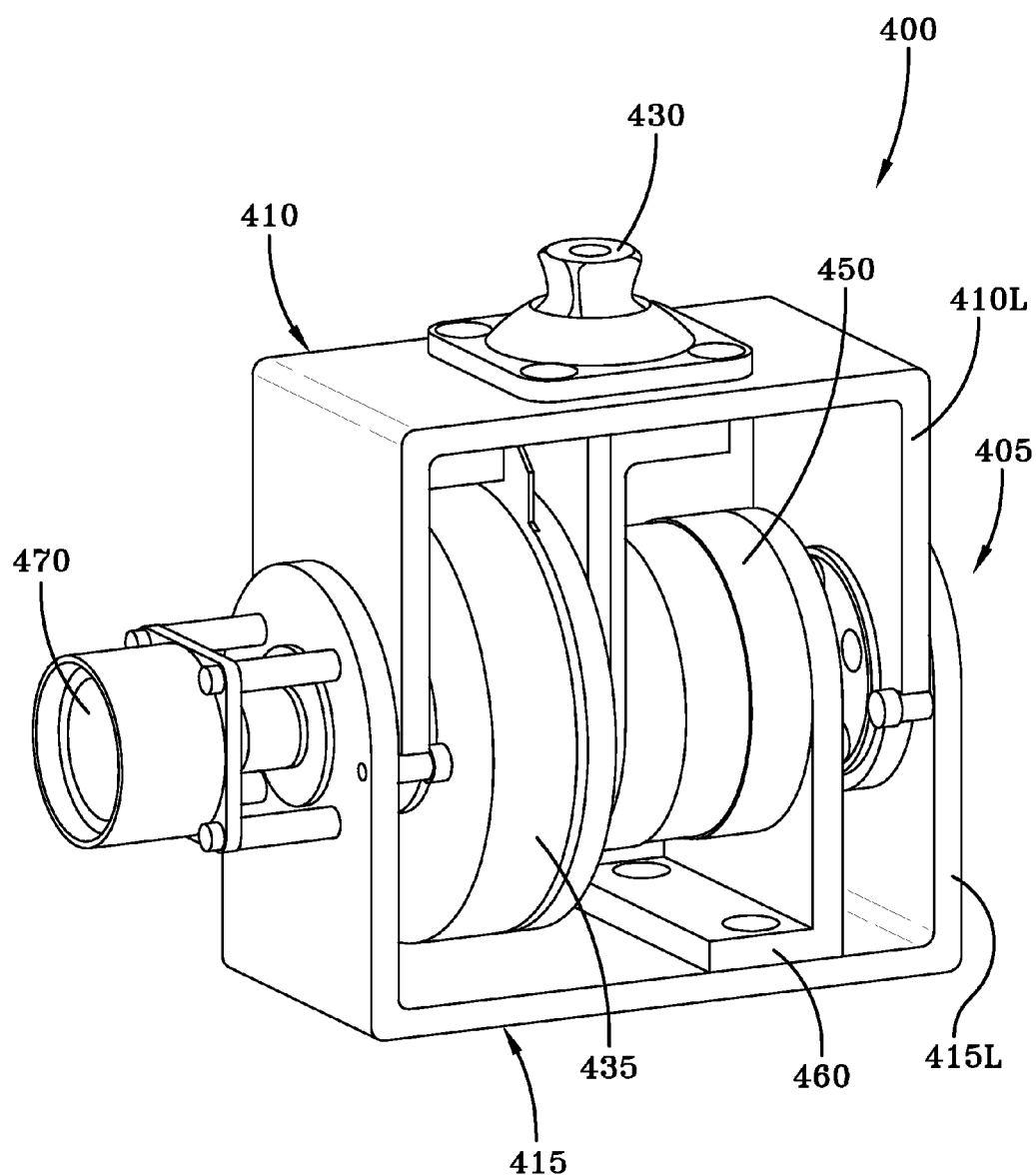
FIG. 9a is a perspective view of an alternate embodiment of an active prosthetic knee joint with regenerative braking that may be used with a prosthetic leg of the present invention, wherein all regulation and control of gait is provided by an actuator/generator.
Figure 9B:
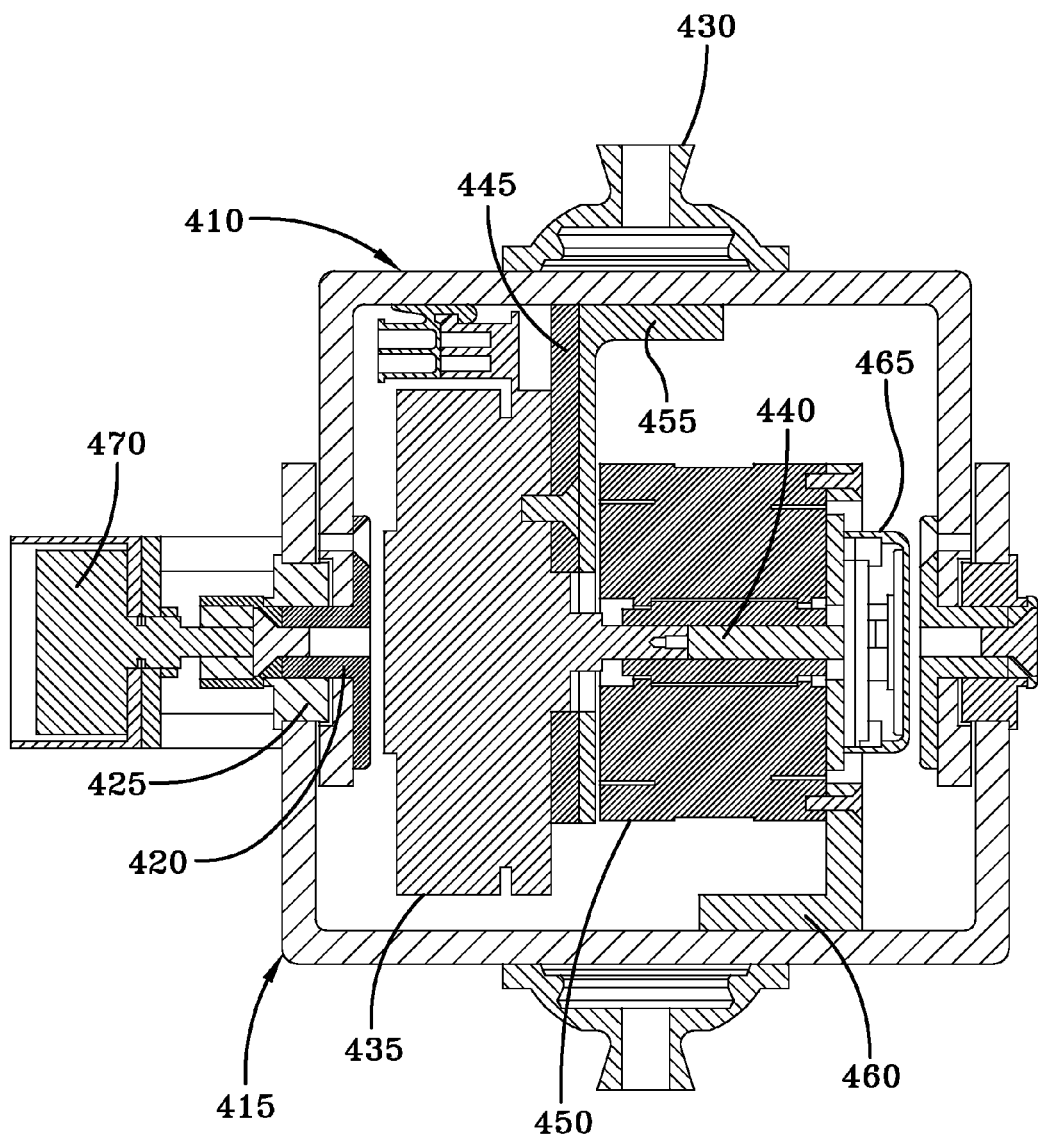

Another embodiment of a regenerative and active prosthetic knee 400 for use with an above knee (AK) prosthetic leg of the present invention is shown in FIGS. 9a-9b. This particular embodiment of the prosthetic knee 400 may be used with a lower frame portion like those shown in virtually any of the previous embodiments.

Like the prosthetic knee embodiment of FIGS. 8a-8b, this embodiment of the prosthetic knee 400 does not require the use of an additional (supplementary) damping device. Rather, the knee 400 makes use of an interlocking and pivoting bracket assembly 405 that resides above the lower leg frame (not shown) and houses an actuator/generator 435 and drive system 450.

As shown in FIGS. 9a-9b, the bracket assembly 405 comprises substantially C-shaped upper and lower brackets 410, 415, although one skilled in the art would understand that other designs could certainly be employed. One of the upper and lower brackets 410, 415 is designed to fit within the extending legs of the other bracket. In this particular embodiment, the upper bracket 410 fits within the lower bracket 415, although the design could be reversed. Each set of overlapping bracket legs 410L, 415L are pivotally coupled, such as by a hinge pin 420 and bearing 425. The coupled brackets 410, 415 form a rotatable assembly wherein the brackets are free to rotate about the hinge pins 420. With one bracket maintained in a fixed position, such as by a prosthetic socket, the other bracket remains free to rotate.

The upper bracket 410 is adapted for attachment to a prosthetic socket, such as one of the prosthetic sockets shown in FIGS. 5-8. The upper bracket could also be adapted for attachment to an implant or some other means of connection to the residual limb of an amputee. Various means of connecting the upper bracket 410 to a prosthetic socket may be employed, such as the pyramid connector 430 shown. The lower bracket 415 is adapted for connection to the lower leg frame. This connection may be accomplished by various known means.

In this embodiment, the actuator/generator 435 is suspended from the underside of the upper bracket 410 by an actuator mount 445, such that the actuator/generator resides within the open space between the upper bracket and lower bracket 415. The actuator/generator 435 used in this particular embodiment of the prosthetic knee 400 is a brushless DC pancake motor, although it may be possible to utilize other types of motors for this purpose.

Similarly, a gear system 450 is suspended from the underside of the upper bracket 410 by a gear system mount 455, such that the gear system resides within the open space between the upper bracket and lower bracket 415. The gear system 450 is coupled to the output shaft 440 of the actuator/generator 435. The gear system used in this particular embodiment of the prosthetic knee 400 is referred to as a twin spin gear system, although it may be possible to utilize other types of drive systems for this purpose. For example, it may be possible to employ one or more harmonic drives to transfer the output of the actuator/generator 435 to the knee 400.

An output bracket 460 is used to also couple the gear system 450 to the lower bracket 415. In this manner, with the upper bracket 410 secured to a prosthetic socket and its position substantially maintained, rotation of the actuator/generator output shaft 440 by the actuator/generator 435 will cause a corresponding rotation of the gear system 450 and the lower bracket 415 that is coupled thereto by the output bracket 460. In turn, rotation of the lower bracket 415 will cause an extension or flexion of the prosthetic leg (i.e., of the lower leg frame about the knee joint 400).

In this particular embodiment of the prosthetic knee 400, the repeated and forced rotation of the joint assembly 405 that inherently occurs during the amputee's gait cycle results in the forced rotation of the gear system 450 and the actuator/generator 435 connected thereto. Forced rotation of the actuator/generator 435 while in generator mode produces electrical energy that can be used to concurrently power an electronic control system and/or other electrical energy consuming devices used by the amputee. Such additional electrical energy consuming devices may include those discussed above, or other compatible devices not specifically named herein. Excess electrical energy may be captured by the regeneration circuitry and stored in one or more electrical energy storage devices for later use. This stored electrical energy can then be subsequently used as needed to power the electronic control system and/or one or more other electrical energy consuming devices as described above. As in previously described embodiments, an even larger amount of electrical energy can be generated when an amputee descends stairs or a slope, as additional energy must be absorbed by the knee joint assembly 405 and is correspondingly transferred to the actuator/generator 435.

Capture, storage, and distribution of electrical energy produced by the regenerative knee 400 is controlled by the electronic control system. Stored electrical energy can subsequently be withdrawn from the electrical energy storage device(s) as needed to power the electronic control system itself, other associated electrical energy consuming devices used by the amputee, and/or to power the actuator/generator 435 in actuator mode when a gait adjustment is needed. The amount, speed, duration, frequency, and other aspects of any gait adjustments are also determined and implemented by the electronic control system.

As with the other embodiments of a prosthetic leg of the present invention, various sensors may be employed to allow for proper monitoring and control of a prosthetic leg employing the knee of FIGS. 9a-9b. In the particular example of FIGS. 9a-9b, an encoder 465 is shown to be attached to the gear system 450 and a goniometer 470 is shown to be rotatably attached to the lower bracket 415 for this purpose. Remote sensors (not shown) may also be employed, and may be variously located about the amputee, such as on the amputee's torso, residual limb, or one or more other limbs. For example, a remote sensor may be located on the foot (e.g., in a shoe) of the amputee's intact leg. Such remotes sensors may send signals to the electronic control system via a wired or wireless connection. In the case of a wireless connection, the electronic control system includes, or is otherwise in communication with, a receiver capable of receiving the output signal from such a remote sensor.

In the exemplary embodiments of a prosthetic knee shown in FIGS. 5-9, it is contemplated that the actuator/generator can be one of various known types of permanent magnet motors. For example, it is possible that the actuator/generator may be an AC, DC brush, or brushless DC type permanent magnet motor. Certain types of motors may offer particular advantages or disadvantages to specific applications. For example, AC motors require no brushes, but also require a sinusoidally varying voltage supply. Thus, it may be difficult and/or inefficient to use an AC motor when power will likely be stored in battery or capacitor type storage devices. However, it may be possible to use such a motor with proper converting electronics installed, and such embodiments are considered to be within the scope of the present invention.

A DC brush motor is a well known and reliable type of permanent magnet motor. Such motors are also simple, comparatively inexpensive, and require minimal control circuitry for basic operation—whether operating as an actuator or as a generator. A drawback of DC brush motors is that brushes are required for their operation. As a result, brush wear may necessitate brush replacement at some point during the life of the motor. The use of brushes also produces electrical arcing that could potentially be dangerous in certain environments. As such, if a DC brush motor is used as an actuator/generator in the present invention, it should be understood that access to the motor may be provided to facilitate brush replacement, and various types of shielding may be used to minimize electrical arcing concerns.

A brushless DC motor is, as the name implies, a DC powered permanent magnet motor requiring no brushes for its operation. Although this is referred to as a DC motor, the DC power on which it operates is actually converted to a form of AC power by an integrated motor control circuit. It is this AC power that is sent to the brushless motor. Thus, such a motor can provide some of the advantages of an AC motor while operating from a DC power source. Because there are no brushes to wear out, brushless DC motors also have a virtually unlimited life expectancy, and have a power density and efficiency that exceeds those of DC brush motors. A problem with using brushless DC motors, however, is that the associated control electronics are more complicated, larger, and more expensive than those required by a DC brush motor. Additional control electronics are also necessary in order to operate a brushless DC motor as a generator.

In general, DC motors operate at high rotational speeds. Therefore, when using a DC motor, it will often be necessary to employ a transmission device, such as a speed reducer, in order to reduce the motor's operating rotational speed at high power outputs to a more usable output speed. Such transmission devices are commercially available with reduction ratios sufficient for use in the present invention. As an alternative to a DC motor and speed reducer assembly, there are also high torque-low speed DC motors in development. This type of DC motor may be ideally suited for use in a prosthetic knee of the present invention, and such is considered to be within the scope thereof.

As can be understood from the foregoing discussion, a variety of different permanent magnet motors may be used as an actuator/generator in embodiments of the present invention. other types of AC and DC motors may also be used, such as for example, field wound motors. Choice of motor type and of other motor specifications will likely be dependent on the particular design of the prosthetic knee, and nothing herein is to be read as limiting the present invention to a particular motor type, size or configuration, or to the use of a transmission device. Further, it is contemplated that non-motor actuators can also be employed, such as those employing piezos.

Figure 10A:
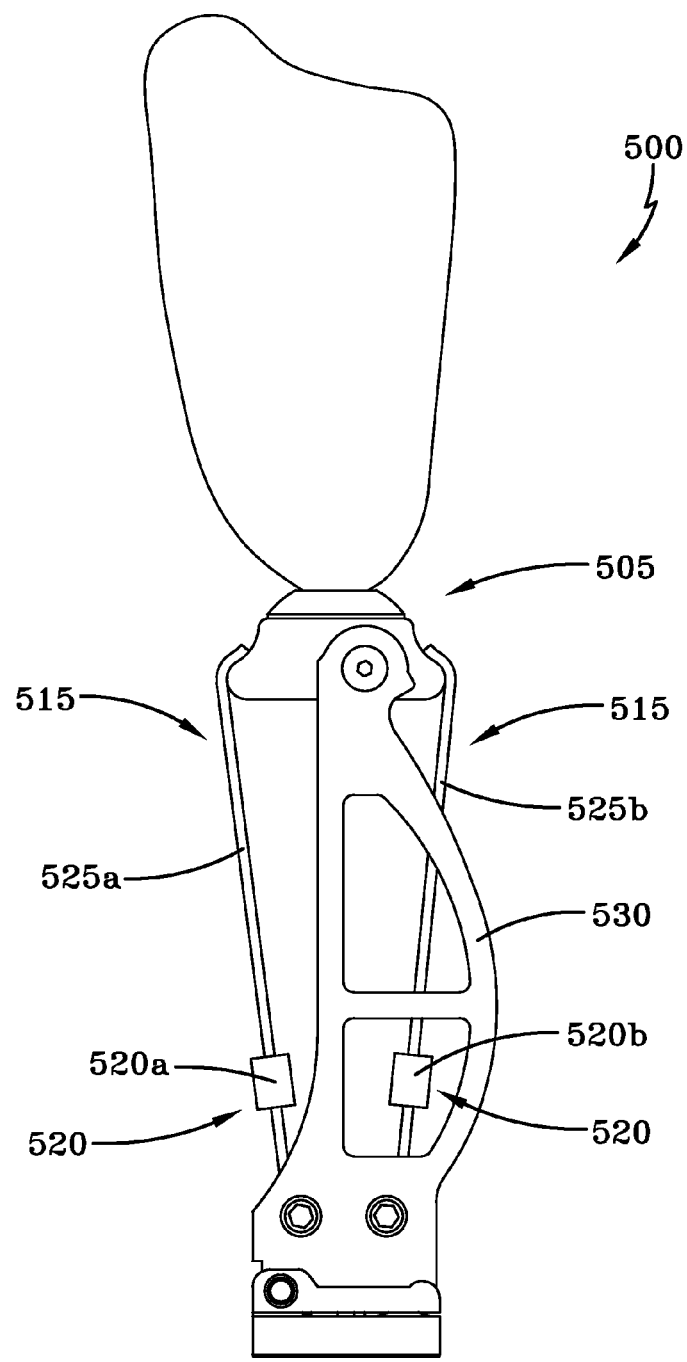
FIG. 10a is a schematic diagram, representing a prosthetic leg having another embodiment of an active prosthetic knee with regenerative braking according to the present invention, wherein an electroactive polymer (EAP) actuator is employed.
Figure 10B:
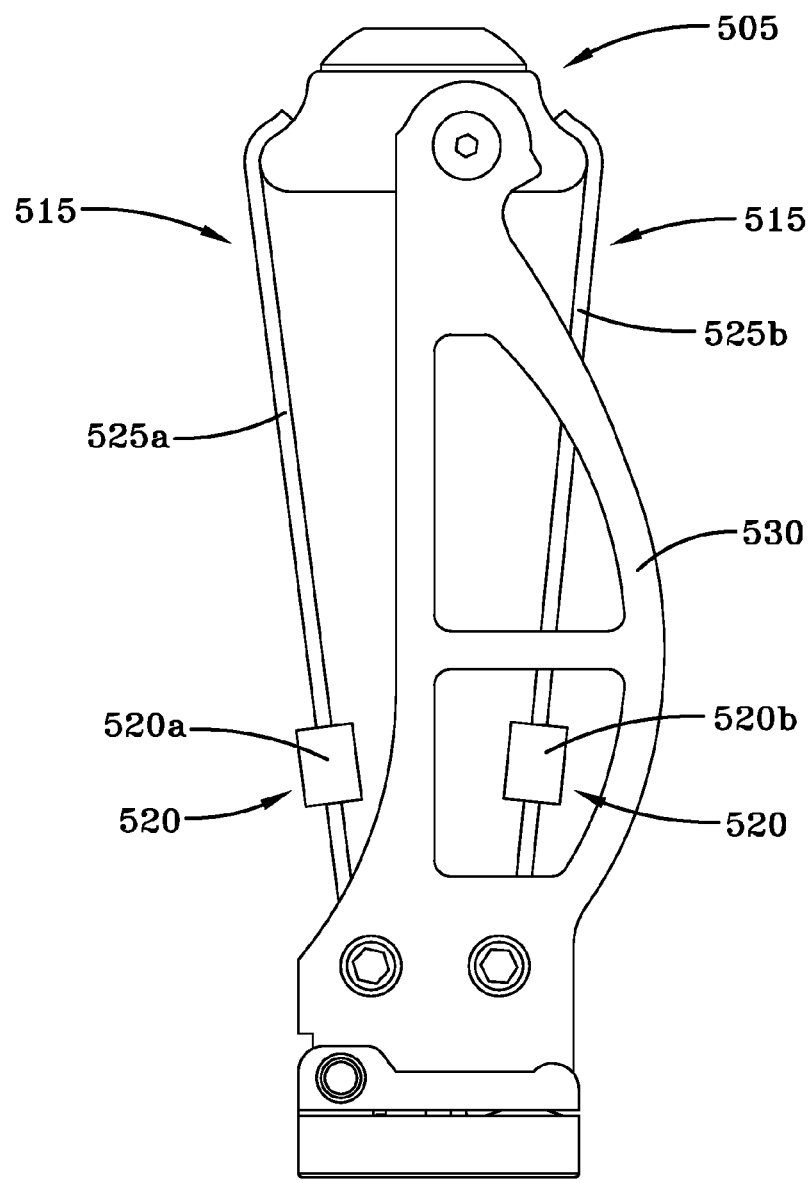
FIG. 10b is an enlarged view of a lower portion of the prosthetic leg and the prosthetic knee of FIG. 10a, wherein an EAP actuator(s) is schematically represented for purposes of simplicity.

Yet another embodiment of an above knee (AK) regenerative and active prosthetic leg 500 of the present invention is shown in FIGS. 10a-10b. This particular embodiment of the prosthetic leg 500 again employs an active and regenerative prosthetic knee joint 505 with a drive assembly 510 having a actuator/generator 520 to provide for gait control, and to actively assist the amputee with various ambulatory activities. However, unlike previously described embodiments of a prosthetic leg, which employed a regenerative knee having some form of a permanent magnet actuator/generator, this embodiment of the prosthetic leg 500 utilizes an electroactive polymer (EAP) as the actuator/generator 520.

Electroactive polymers (EAP's) are typically formed from various conducting polymer materials or assemblies of such materials. These actuators change shape when an electrical field is applied thereto. Depending on their mounting and interactions with the environment, this change in shape can be accompanied by an exertion of some amount of force. A particularly interesting type of EAP is referred to as a dielectric polymer, although an EAP actuator of the present invention is not limited to any particular EAP class. Dielectric EAP actuators function much like traditional capacitors—storing electrical energy and charge in a capacitive field. Consequently, they can provide the regenerative function required by the present invention.

By controlling the shape of the EAP and the location and magnitude of the electrical field applied thereto, deformation of the EAP can also be controlled. For example, an EAP element may be constructed and an electrical field applied thereto such that the EAP is made to extend or retract (stretch and compress) a predetermined distance with a predetermined amount of force. Therefore, by selecting the proper EAP material, size, and shape, it can be seen that an EAP actuator can be constructed that can be used as an actuator/generator in the present invention. EAP actuators are of interest for use in a prosthetic knee of the present invention for several reasons, including without limitation: their light weight; their noiseless operation; their ability to exert a force that is many times their own weight; their fast response time; their inherent compliance, which can allow for EAP actuator designs that mimic actual muscle; and the fact that application of a specific voltage to an EAP actuator produces a specific level of actuation—resulting in an actuator position that can be maintained against a counter force without a further expenditure of energy (which is not possible with a permanent magnet motor).

In the prosthetic knee of FIGS. 10a-10b, the electroactive polymer actuator (actuator/generator) 520 is schematically represented for purposes of simplicity. As can be seen, there are actually two EAP actuators 520a, 520b in this embodiment, one end of each attached to the pivoting or rotating knee joint 505 by means of a connecting element 525a, 525b. An opposite end of each EAP actuator 520a, 520b is connected to a frame 530 or similar structure that forms all or a part of the lower prosthetic leg. In this simplistic example, the knee joint 505 is depicted as a simple pulley-type device, although it should be realized that an actual prosthetic knee joint may be considerably more complicated.

In operation, a voltage is applied to one or both of the EAP actuators 520a, 520b to effectuate a rotation of the knee joint 505 in a desired direction. For example, if a contraction-inducing voltage is applied to the EAP actuator 520b, the knee joint 505 will rotate clockwise (unless a balancing contraction is produced in the opposite EAP actuator 520a). The speed of rotation can be controlled by the rate at which the electrical field is applied to the activated EAP actuator and by the resistance to rotation produced by the opposite EAP actuator. Obviously, a voltage could also be applied to both EAP actuators 520a, 520b to better control movement of the knee joint 505, with the magnitude and result of the voltage application varying between the actuators.

As mentioned above, once a voltage has been applied to an EAP actuator, the position thereof can be maintained against a counter force without a further expenditure of energy. As such, an actuator/generator comprised of an EAP actuator can produce a "catch state," a condition where the actuator/generator is essentially in a locked position without a voltage applied thereto. This is not possible when the actuator/generator consists of a permanent magnet motor.

Various EAP actuator designs may be possible for use as a actuator/generator in the present invention. For example, an EAP actuator may be formed from a multitude of thin EAP material layers that are clamped or otherwise held together to form an actuator of desired power output. Alternatively, an EAP actuator may be formed from a unitary continuous film of some thickness. Other designs, such as various gel based EAPs, are also possible and considered within the scope of the present invention, whether presently known or yet to be developed as the EAP art progresses.

In each embodiment of the present invention, an electronic control system is provided to assist with controlling the amputee's gait, and to manage the conversion, storage, and discharge functions of the prosthetic knee's electrical power regeneration system. There have been countless papers and other writings on methods of prosthetic knee control, and the prosthetic leg and associated electronic control system may make use of some or all of these methods.

Figure 11:
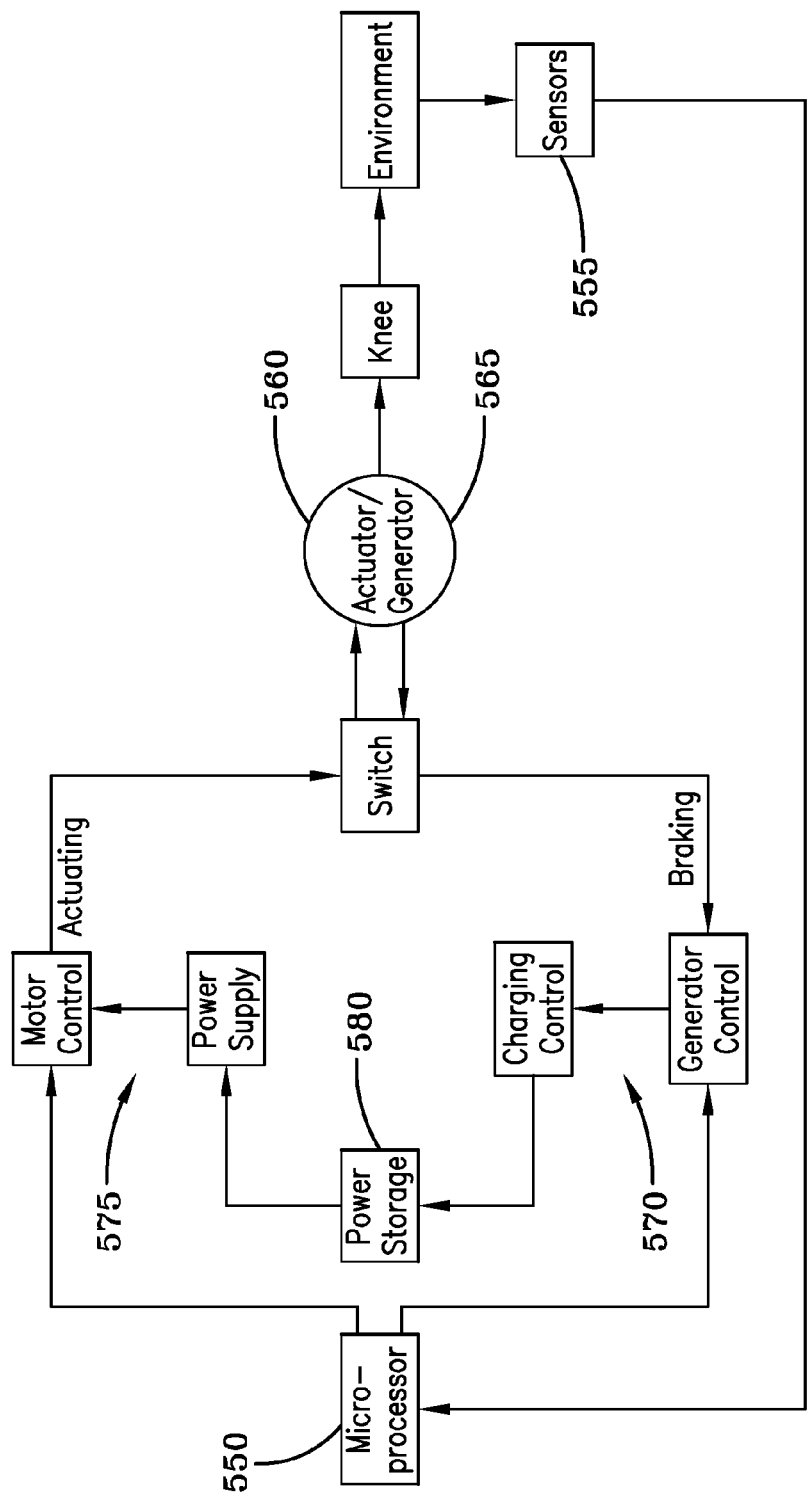
FIG. 11 is a schematic diagram illustrating the general concept of the design and operation of a prosthetic leg with a regenerative knee according to the present invention.
Figure 12:
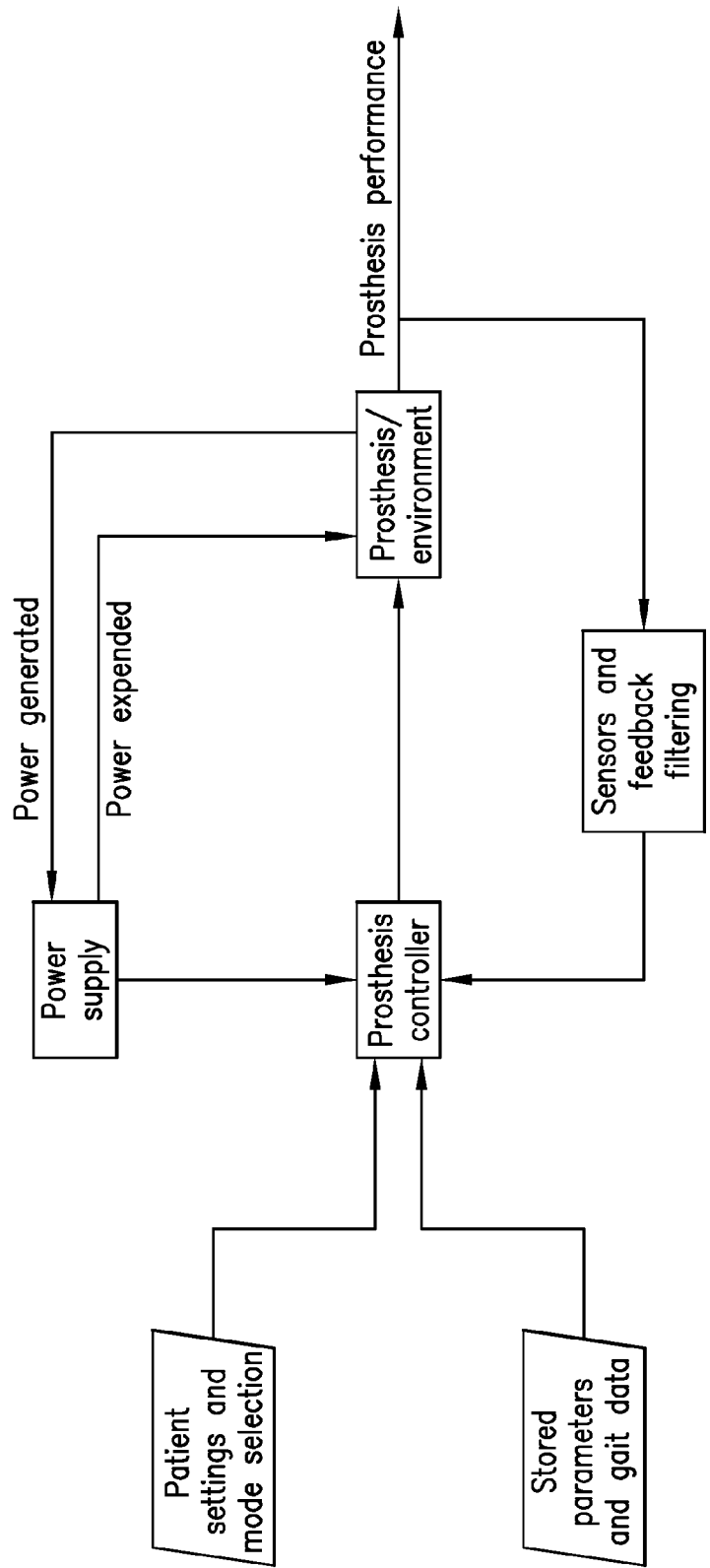
FIG. 12 is a block diagram representation of the function of one embodiment of an electronic control system associated with a prosthetic leg with a regenerative knee according to the present invention.

A general overview of a possible prosthetic leg control system of the present invention is schematically represented in FIGS. 11-12. As shown, a microprocessor 550 receives signals from one or more sensors 555. The sensors 555 may measure conditions relating to the prosthetic leg and to the environment in which it is operating. The sensors 555 may also communicate with an actuator/generator 560. The actuator/generator 560 is coupled to a torque converter 565 (e.g., a ball screw or gear drive) which can be used to actively operate the knee joint of the prosthetic leg, and which may also function with the actuator/generator to produce electrical energy. When the actuator/generator is operating in generator mode 570 (i.e., when the knee joint is resisting or braking against extension or flexion), electrical energy may be sourced to one or more storage devices 580 or to other electrical energy-consuming devices as determined by the microprocessor 550 portion of the electronic control system. When the actuator/generator is operating in actuator mode 575 (i.e., when the knee joint is actively operated to add energy to the amputee's activity), the microprocessor 550 may cause electrical energy to be drawn from the storage device(s) 580 and supplied to the actuator/generator 560.

As with known control systems, the prosthetic leg of the present invention may make use of a plurality of various sensors, which may be mounted to different portions of the prosthetic knee/leg, or to assorted locations on the amputee's body—including the amputee's contralateral leg or foot. These sensors may be used to monitor conditions such as, without limitation: muscle activation (EMG); forces or torques, such as may occur during the stance phase of gait; leg position; knee angle; and leg acceleration. Many other conditions may also be monitored to ensure the prosthetic leg provides for a proper and/or desired gait. As depicted in FIG. 11, the electronic control system of the present invention preferably employs a microprocessor-based controller to perform its various functions. Of course, a PLD or other device capable of supporting configurable code or gates can also be use for the purpose.

The electronic control system is responsible for distributing the electrical energy produced by the actuator/generator of a regenerative prosthetic knee of the present invention to one or more electrical energy consuming devices used by the amputee. As described previously, these devices may be associated with the prosthetic leg or may be unrelated devices used by the amputee. The electronic control system is also responsible for transferring excess electrical energy produced by the actuator/generator while in generator mode to one or more electrical energy storage devices (e.g., a battery, capacitor, or some combination thereof), and for subsequent distribution of the stored electrical energy to the electronic control system itself, or to one or more electrical energy consuming devices associated with the prosthetic leg.

Because a motor-based actuator/generator may produce power over a wide range of voltages (with respect to that of the storage device(s)), particularly during fast movements, the electronic control system is preferably also capable of efficiently converting the voltage associated with the electrical energy to another voltage prior to storage. The electronic control system is also responsible for discharging electrical energy from the storage device(s) to power its own components, to power the actuator/generator while in actuator mode, such as when the actuator/generator actively assists the prosthetic knee in controlling the gait cycle or climbing stairs, for example, and to power one or more ancillary electrical energy consuming devices that may be worn by the amputee. These ancillary devices may or may not be directly related to the prosthetic limb and may include, for example; those devices mentioned above; remote sensors; prosthetic arms, hands, or ankles; or remote interfaces for such devices. Certainly, other electrical energy-consuming devices may also be included, and the foregoing listings are not to be interpreted as limiting the present invention to those devices named therein.

With respect to control of the prosthetic knee, it should be realized that the voltage on a motor typically corresponds to the speed of the motor, and current through a motor typically corresponds to the torque of the motor. Consequently, when a traditional electric motor-based (i.e., non-EAP) actuator/generator is used to operate the prosthetic knee, either torque or speed may be controlled by monitoring such and selecting the respective signal for feedback to the controller.

An electronic control system of the present invention can be designed to selectively operate a prosthetic leg in a variety of modes. Certain of these modes of operation may be directed to achieving a particular gait or to operating the prosthetic leg in a specific manner, without particular concern for energy consumption. Contrarily, certain other modes of operation may be concerned primarily with assuring that an adequate level of stored electrical energy is maintained. It is possible to produce a prosthetic leg having an electronic control system that operates in only a single mode but, preferably, the electronic control system of the present invention is adaptive and can operate the prosthetic leg in a mode selected by the amputee or in a mode automatically selected according to the amputee's activity level and/or external environmental conditions.

Specific modes in which the control system may operate the prosthetic leg can include, without limitation, a maximized regeneration mode, a gait profile duplication mode, and an audible noise minimization mode. The controller may function, or be caused to function, such that the leg is continually operated in a particular mode as long as possible, or the controller may switch, or be caused to switch, between modes.

In a maximized regeneration or highly regenerative operating mode, the knee acts substantially only to reduce or resist (bending) motion in the extension or flexion directions. Consequently, an actuator/generator associated with the knee only absorbs energy (i.e., operates in generator mode); it never expends energy (i.e., operates in actuator mode). There are several control paradigms that can result in a mode of knee control that will achieve this goal, and the use of a microprocessor makes it possible to include a range of control options at the design stage so that selection of a specific mode of control is possible after an amputee has been evaluated.

There may be several sub-modes of operation within a highly regenerative operating mode of the present invention. These sub-modes may include, for example: (1) a sub-mode wherein a fixed knee flexion torque value is set based on heel rise, and a fixed knee extension torque value is set based on the time it takes for the knee to reach full extension at some specified amount of time prior to heel contact; (2) a sub-mode that allows the knee to travel in free swing until it approaches a specified limit in heel rise angle, at which time the controller would cause the actuator/generator to absorb the energy in the flexion swing over a relatively short distance; (3) a sub-mode where the resistance to motion produced by the actuator/generator and/or other damping device is proportional to the speed of the knee, and the flexion and extension settings are based on the heel rise angle and the timing of the terminal impact, respectively; (4) a sub-mode that monitors the energy in the knee swing and keeps it below some predetermined value based on the position of the knee in the heel rise or free swing phases; and (5) a sub-mode that actually modifies the gait trajectory in a manner that forces the amputee to work harder during ambulation, thereby potentially increasing the energy available for recovery and use.

It should be noted that when sub-mode (2) is employed, it is contemplated that the controller would subsequently allow the knee to swing back in free swing until it approaches full extension—at which time the knee would again absorb the energy from terminal impact. When sub-mode (5) is employed, it has been discovered that limiting the angle of the knee in heel rise provides one means by which the amputee can be caused to exert more effort during ambulation. More specifically, limiting the angle of the knee in heel rise increases the effective moment of inertia (MOI) of the prosthetic leg by forcing the weight of a lower portion of the leg further away from the hip, thereby increasing the amount of effort required to move the leg (and knee) through the gait cycle.

With further respect to sub-mode (5), it may also be possible to select between producing a gait profile that provides greater energy generation, and a gait profile that exercises the amputee. As these objectives may be related, although not necessarily the same, it can be understood that the modes of control may be similar.

It should also be noted that use of the above-described sub-operating modes can be mixed. For example, it is possible to control heel rise by setting a fixed torque value for knee flexion (i.e., as in sub-mode (1)), and to then allow the knee to swing back freely for most of the return swing (i.e., as in sub-mode (2)). In this manner, the knee can most quickly be moved out in front of the amputee, thereby improving the amputee's stability.

With respect to maximizing the regenerative capabilities of such a prosthetic leg, several considerations should be noted. First, it has been determined that the amount of electrical energy generated by a prosthetic leg with a regenerative prosthetic knee of the present invention is affected by how the amputee uses the prosthesis. More specifically, it can be seen from the graph of FIG. 2 that the amount of power generated by such a knee increases exponentially with gait speed. Thus, while there is a great deal of energy available at high gait speeds, there is substantially less energy available at low gait speeds. Because friction must also be accounted for, simple modeling proves that there will always be some minimum gait speed below which a particular regenerative knee will no longer be able to remain self-sustaining. That is, there will always be some minimum gait speed below which a particular regenerative knee will no longer generate more electrical energy than it uses. Consequently, it is evident that while it may be possible to create a prosthetic leg having a regenerative knee that generates a surplus of electrical energy under normal usage, it is still nonetheless important to limit as much as possible the inefficiencies of the various mechanical and electrical devices associated with the prosthetic leg.

Further consideration of the rules under which a regenerative knee can operate reveals that there is a range of possible functions and goals that can be modified to adapt to the current state of the power supply. At one extreme, a regenerative prosthetic knee of the present invention can function in a simplified mode, wherein its operation is governed by one of the highly regenerative sub-modes described above. In this case, the knee would consume little power, and would generate significant amounts of electrical energy. At the other end of the spectrum, a highly active patient whose gait causes the regenerative knee to produce a significant amount of electrical energy even at a normal walking speed, might be better served by a control scheme that optimizes one of the parameters mentioned above, or otherwise transports excess electrical energy to another electrical energy consuming device.

A difficulty lies in finding a proper balance between these two operating extremes. For example, when the controller is not forced to function under a particular operating sub-mode, it must be able to determine what function to optimize when there is a surplus of available electrical energy, and what function to compromise when there is a shortage of available electrical energy. As can be understood by one skilled in the art, this is not an easy task. Preferably, the control system of the present invention is not limited to simply selecting between one maximized regeneration sub-mode or another. Rather, the control system of the present invention is preferably able to adjust operation of the regenerative knee using a sliding scale that takes into consideration the current state of the overall system. This overall state may be defined by one or more parameters such as, for example, the amount of energy stored in an electrical energy storage device, the condition of the patient, and the current task that the patient is attempting to accomplish. Other parameters may also be considered. To this end, the control system is also able to monitor how well the selected goals are being adhered to. In this way, the controller evaluates how well a functional goal, or some combination of functional goals, is being adhered to. The controller then determines the adjustments that must be made to the control strategy in order to strike a proper balance between different control modes and to achieve the desired functional goal, or goals.

Several feedback modes may be employed with respect to monitoring and controlling the amount of electrical energy available to operate the prosthetic leg. In a first mode, there is essentially no feedback. In this mode, the amputee sets the type and level of desired performance he/she wants from the prosthetic leg and the control system simply reports the status of the power supply (i.e., the electrical energy storage device(s)) to the amputee. In a second feedback mode, the control system monitors the state of charge of the power supply and adjusts the control scheme to react to such state of charge. For example, a total charge indication of 25% might result in a gait that charges the storage device(s) fairly quickly, while a charge indication of 90% might instead result in a very high level of optimization of one or more of the above-mentioned gait parameters. In yet another feedback mode, the control system monitors the state of electrical energy flowing to the power supply and attempts to produce a state of zero energy consumption over some specified period of time. In this feedback mode, the control system essentially tries to keep the power supply fully charged at all times so that there is ample electrical energy available to assist the amputee with energy intensive functions such as, for example, stair climbing.

The control system may also operate the prosthetic leg in a gait profile duplication mode. In this operating mode, the focus of the control system is to operate the prosthetic leg in a manner that mimics some predetermined gait profile. From a mathematical/control point of view, gait profile may be defined in a number of ways. For example only, gait profile may be determined by observing and controlling: (1) the time course of the knee angle as a function of fractional stride time where the fractional stride time is defined as the time since some specific event in the gait cycle, such as heel strike or toe off, has occurred, divided by the overall stride time (i.e., $[(T-T_{ref})/(T_{stride})]$; (2) the time course of the knee angle as a function of the knee's position, speed, and acceleration over the course of a stride; and (3) knee angle as a function of hip position, speed, and acceleration over a single stride. Certainly, there are a multiplicity of other methods by which gait profile may be defined, and such methods would be understood by one skilled in the art. Consequently, the above methods are provided for illustration only, and the present invention is in no way to be considered limited to the use thereof.

In light of the foregoing, it is evident that the control system can be programmed to produce virtually any gait profile. However, as a natural gait profile is likely to be a very desirable profile for many amputee's, such will be discussed as an example of a specific gait profile below. A natural gait profile is, of course, a gait profile that mimics the natural gait of a non-amputee. Thus, this mode of operation attempts to operate the prosthetic leg in a manner that will most accurately produce a gait like that which would be exhibited by the amputee if he or she was still in possession of both natural legs. It should be noted that while the goal in this case is to achieve a natural gait, the actual gait resulting from this mode of operation may differ somewhat from the gait of a non-amputee because the mechanics of the ankle and other parts of the prosthetic leg may not allow for perfect duplication. However, the gait profile chosen is targeted to make the gait cycle look as close as possible to natural or "normal" gait.

This form of gait control is arguably the most aesthetically appealing, since it essentially minimizes the degree to which the amputee's disability can be recognized. Further, a natural gait may also decrease the various torques and other forces of interaction between the socket and the amputee's residual limb. It can also be shown that a prosthetic leg with a regenerative knee of the present invention that is operated in a manner that mimics natural gait will generate a surplus of electrical energy under most conditions for many patients. For these reasons, operating the prosthetic leg in a manner that mimics natural gait results in a good balance of the desirable traits involved with a prosthetic gait.

A substantially natural gait can be achieved in several ways. One method is by forcing the prosthetic limb to follow a stored profile of a known natural or normal gait cycle. Such a profile can be based on measured data taken from a test subject of similar stature and mobility. Such a profile may also be calculated. A natural gait can also be achieved by instrumenting the amputee's natural leg and forcing the prosthetic leg to duplicate a time scaled version of the trajectory detected for the previous stride of the natural leg. A control scheme that combines these methods may also be used to produce a natural gait in the amputee.

Under certain conditions, however, it has been determined that mimicking natural gait can result in energy consumption instead of energy generation. The actual energy balance will depend on the inefficiencies of the prosthesis, and other variables such as the speed at which the amputee is walking or running, and the terrain being traversed. Thus, when energy consumption is detected by the control system, there must be some shifting between the goal of mimicking natural gait and one of regeneration. Thus, under these circumstances, the control system preferably shifts into, or slides toward, the regeneration mode of operation so as to balance power consumption in a manner that is still suited to the amputee's desired pattern(s) of usage.

It has been found that an efficient way of achieving this balance is to limit the gain of the actuator/generator in a non-symmetric manner. In this mode of control, the gain and/or maximum torque values associated with the actuator/generator can be limited when it is expending energy, such as when it is attempting to accelerate heel rise. Contrarily, the gain and or maximum torque values can remain high when the resulting torque results in braking and, consequently, energy generation.

At the extreme end of this design, the gain or maximum torque values associated with the actuator/generator when operating in a manner that expends energy would be set to zero (0), and the knee would simply act as a regenerative knee such as that previously described. A key point in such a control scheme is to keep the gain of the braking forces produced by the actuator/generator high enough to limit heel rise and terminal impact. By doing so, the knee can not fall behind as long as the frictional forces associated therewith are low enough for the energy transmitted from the hip to the shin and foot to overcome during the swing phase of the gait cycle.

Another method for achieving a balance between energy consumption and mimicking natural gait is to scale heel rise to some value between the natural profile and a smaller angle and to thus force the amputee's hip to work harder. It is then possible to absorb much of this additional energy at the knee. One means of producing this result is to keep the controller gains and maximum torques constant, but scale the trajectory of the heel rise between that of a natural gait profile, and a profile that has a maximum heel rise just larger than is necessary to cause the foot to clear the floor as the shin swings through.

It is also possible for the controller to operate the prosthetic leg in an audible noise minimization mode. As amputees commonly complain about the noise of prosthetic devices, it is desirable to enable the prosthesis to operate as quietly as possible when an amputee so elects.

In the case of an electric motor-powered knee mechanism, much of the generated noise can be attributed to the speed of the associated actuator device (e.g., a ball screw). Consequently, it has been found that if the knee is forced to follow a path of reduced angular travel at a near constant speed, the knee will achieve speeds near the minimum peak knee speeds necessary for proper knee operation, but with minimal actuator noise at a given gait speed.

This can be accomplished by various techniques. One such technique is to predetermine the degree of knee flexion necessary to allow safe swing through of the prosthetic leg and then limit the knee angle to some small margin of error above this value. If the stride time is known, it is then possible to determine the time required for the prosthetic leg to reach the point where it will contact the floor, and to set the knee speed so that it is as close to constant over the entire stride as possible. This will allow the knee to be set to the minimum angular speed possible for the corresponding speed of gait.

The peak accelerations corresponding to the given knee speed also need to be set to minimize the gear torques and forces. This will minimize the noise caused by the forces acting on the gears as apposed to the noise caused by the speed of the gears. While not technically a sliding scale type adjustment from normal gait, in most situations, keeping the knee straighter at a given walking speed will result in an increase in the moment of inertia of the leg as seen by the hip and will consequently result in more work being performed by the amputee at the hip as discussed with respect to regeneration sub-mode (5), above. This can actually increase the amount of electrical energy that can be generated by the knee in comparison to that which can be produced during normal gait. As such, this mode of operation may actually be a preferred mode of gait for healthy amputee's who can produce the additional energy expenditure at the hip and who may have a uses for an additional amount of generated electrical energy.

Another method of minimizing audible noise is to always maintain some minimum torque on the actuator/generator assembly. This functions to prevent noise associated with the mechanical lashes and tolerances of the mechanical devices in the drive train. The torque can either resist or assist the patient's motion. As such, a goal of this control scheme is to eliminate any portions of the knee trajectory wherein the knee is substantially in a "free swing" condition.

Figure 13:
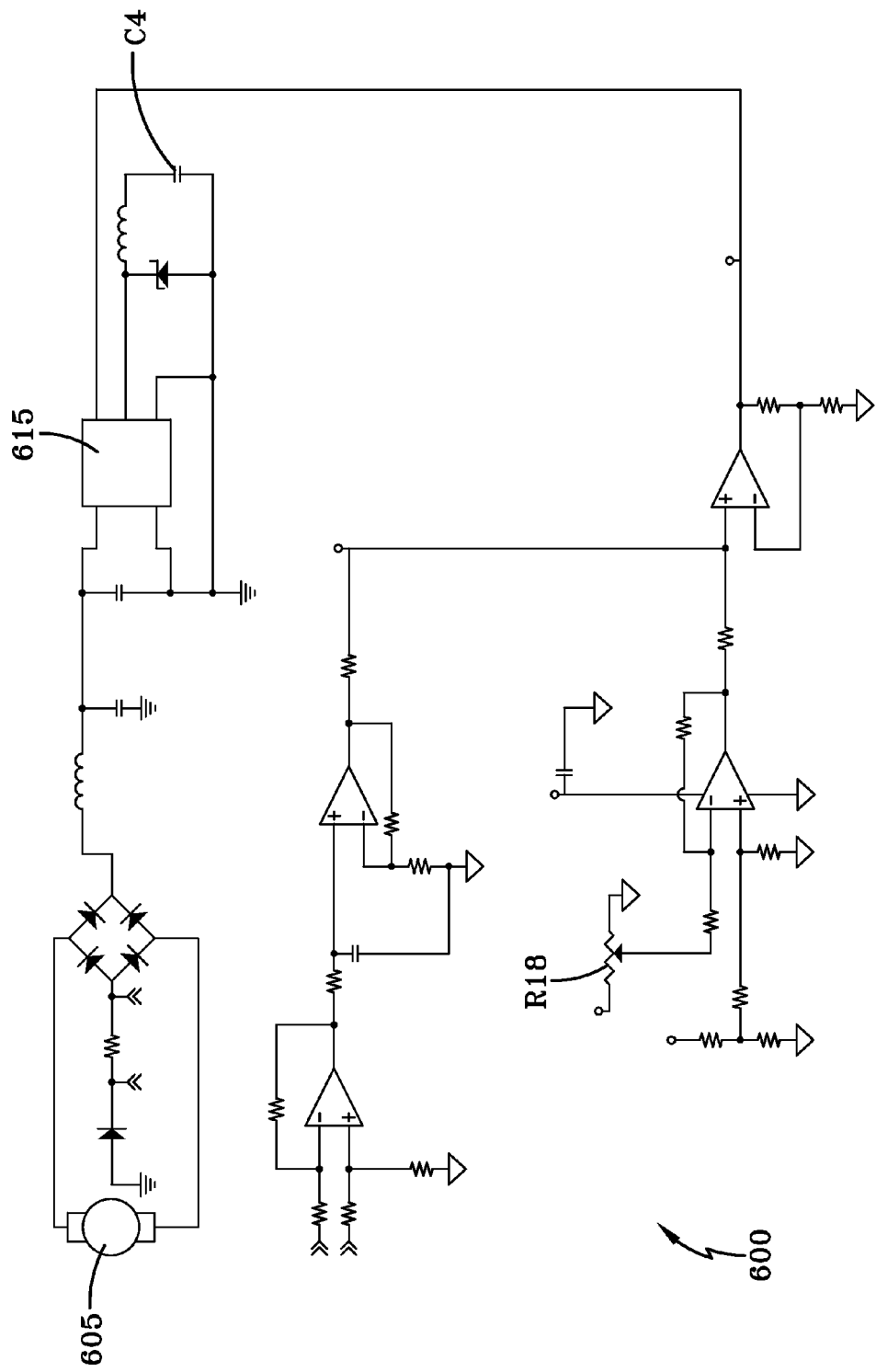
FIG. 13 illustrates one exemplary embodiment of an electrical energy regeneration control circuit that may be used with a prosthetic leg with a regenerative knee according to the present invention.

An exemplary regeneration circuit 600 that may form a portion of a prosthetic leg of the present invention is depicted in FIG. 13. One skilled in the art will realize that a useable regeneration circuit may be constructed in any number of ways and, therefore, it is not intended, nor should it be interpreted, that a regeneration circuit of the present invention is limited to the embodiment thereof shown in FIG. 13.

As shown, the exemplary regeneration circuit 600 employs an actuator/generator 605 torque controller. In this particular embodiment of the regeneration circuit 600, actuator/generator torque is set at the resistor labeled as R18. In operation, electrical power is drawn from the actuator/generator 605 while the actuator/generator is operating in generator mode, and is subsequently stepped down to the voltage currently present across the capacitor labeled as C4. Once this step-down has occurred, the electrical power is fed to the capacitor C4. It should be noted that a capacitor was used for the output in this particular example of the regeneration circuit 600 only to demonstrate the ability of the circuit to function efficiently across a wide range of output voltages. As such, it is not to be interpreted that the regeneration circuit 600 shown, or another useable regeneration circuit, must be so constructed.

Feedback for this particular control circuit 600 is obtained in a novel manner. That is, rather than feeding back the output voltage as is done in conventional switching or switch mode regulator circuits, or feeding back the output current, as is done in less common current sources—this circuit controls the current input to the switching regulator 615. This is a useful distinction because it is the current output of the actuator/generator that determines the torque produced thereby. Thus, by using a switching topology such as that shown in FIG. 13, a torque controller can be constructed that not only provides precise control of the actuator/generator torque, but also efficiently converts absorbed mechanical energy into electrical energy that can subsequently be stored. This configuration uses a buck or step down configuration. However, the same principal can be applied to boost/step up, buck/boost, SEPIC, or even linear regulators to allow the precise control of actuator/generator torque. Usage of one of the mentioned switching or switch mode regulator topologies also provides efficient DC-DC conversion for energy storage.

It should be realized that while several exemplary embodiments of prosthetic legs and/or regenerative prosthetic knees and of control systems and control schemes relating thereto have been described above, various alternative designs may also be available to one skilled in the art. For example, a plurality of different frame designs and damping devices may be used. Additionally, while it is described above that an actuator and generator are generally combined into a single actuator/generator device, it should be understood that the actuator and generator may actually be separate devices. It should also be realized that there are numerous regenerative and/or electronic control circuits that may be designed and implemented, and nothing herein should be interpreted as limiting the present invention to any specific design or construction. Consequently, it would be understood by one skilled in the art that various mechanical and/or electrical modifications may be made to the exemplary embodiments presented herein while still falling within the scope of present invention.

In addition, it is also possible to construct a prosthetic leg with a regenerative knee wherein the actuator/generator and an electrical energy storage device or devices are not in communication with each other and, therefore, the electrical energy storage device(s) is not recharged by the actuator/generator. In such a system, power for the electronics can be drawn from the actuator/generator during those times when the actuator/generator is generating electric power. It is also possible that lower power demanding tasks such as, for example, running a microprocessor and its associated sensors, could simply be delegated to the electrical energy storage device(s). It is also generally possible to limit the times during which high power demanding tasks are performed to those times where the actuator/generator is able to generate electric power, thereby minimizing any additional drain on the electrical energy storage device(s). While the electrical energy storage device(s) might not be recharged by the actuator/generator in such an embodiment, the electrical energy storage device(s) could at least be reduced in size by eliminating or reducing the need to draw power therefrom for high power demanding tasks.

As such, while certain embodiments of the present invention are described in detail above, the scope of the invention is not to be considered limited by such disclosure, and modifications are possible without departing from the spirit of the invention as evidenced by the following claims:

What is claimed is:

1. A prosthetic leg having a regenerative knee, comprising:
   a frame;
   a knee joint;
   a damping device connected between said frame and said knee joint, said damping device operative to adjust the gait of a user;
   an actuator/generator associated with said knee joint;
   at least one electrical energy storage device in communication with said actuator/generator;
   at least one sensor for monitoring and reporting at least one condition of said prosthetic leg; and
   an electronic control system in communication with said damping device, said actuator/generator, said at least one electrical energy storage device, and said at least one sensor;
   wherein bending of the knee joint during ambulation of a user causes a forced movement of said actuator/generator and the subsequent generation of electrical energy;
   wherein said electronic control system adjusts said damping device as needed to regulate the gait of said user; and
   wherein said electronic control system is operative to distribute electrical energy to one or more electrical energy consuming devices associated with said prosthetic leg and transfers excess electrical energy produced by said actuator/generator to said at least one electrical energy storage device for later use.

2. The prosthetic leg of claim 1, wherein said damping device is selected from the group consisting of hydraulic cylinders, pneumatic cylinders, and magneto-rheological fluid employing dampers or brakes.

3. The prosthetic leg of claim 1, wherein said actuator/generator is selected from the group consisting field wound and permanent magnet motors.

4. The prosthetic leg of claim 1, wherein said at least one electrical energy storage device is selected from the group consisting of batteries and capacitors.

5. The prosthetic leg of claim 1, wherein said electronic control system controls operation of said prosthetic leg by setting a fixed knee joint flexion torque value based on heel rise, and a fixed knee joint extension torque value based on the time required for said knee joint to reach full extension at some specified amount of time prior to heel contact.

6. The prosthetic leg of claim 1, wherein said electronic control system controls operation of said prosthetic leg by allowing said knee joint to swing freely in flexion until it approaches a specified limit in heel rise angle, at which time said control system causes said actuator/generator to absorb energy from the flexion swing, said control system subsequently allowing said knee to swing back freely until it approaches full extension, at which time energy is absorbed from terminal impact.

7. The prosthetic leg of claim 1, wherein resistance to motion produced by said actuator/generator and/or other damping device is proportional to the angular speed of the knee joint, and wherein said electronic control system controls operation of said prosthetic leg by creating flexion and extension settings based on heel rise angle and the timing of terminal impact, respectively.

8. The prosthetic leg of claim 1, wherein said electronic control system controls operation of said prosthetic leg by monitoring the amount of energy produced by rotation of said knee joint and maintaining said amount of energy below some predetermined level based on the position of said knee joint in a heel rise or free swing phase of said user's gait cycle.

9. The prosthetic leg of claim 1, wherein said electronic control system controls operation of said prosthetic leg by modifying said user's gait trajectory in a manner that forces said user to work harder during ambulation, thereby increasing the amount of energy available for recovery and use.

10. The prosthetic leg of claim 9, wherein said electronic control system acts to limit the angle of said knee joint during heel rise.

11. The prosthetic leg of claim 1, wherein said electronic control system controls operation of said prosthetic leg by some combination of the methods of claims 5-9.

12. The prosthetic leg of claim 1, wherein said electronic control system controls operation of said prosthetic leg using a sliding scale that takes into consideration one or more of the current state of charge of said at least one electrical energy storage device, an amount of energy being output by said user, and the type of terrain being traversed.

13. The prosthetic leg of claim 1, wherein said electronic control system controls operation of said prosthetic leg by setting said damping device to limit both heel rise and terminal impact to some predetermined and corresponding range of values, and leaving said setting unchanged unless a change in gait produces a change in heel rise angle or terminal impact timing that falls outside of said range.

14. The prosthetic leg of claim 1, wherein said user manually sets said prosthetic leg to operate in a particular manner and said electronic control system simply reports the charge status of said at least one electrical energy storage device.

15. The prosthetic leg of claim 1, wherein said electronic control system continually monitors the charge status of said at least one electrical energy storage device and correspondingly adjusts operation of said prosthetic leg in a manner that results in a greater or lesser amount of electrical energy generation by said actuator/generator.

16. The prosthetic leg of claim 15, wherein when said charge status falls below some predetermined level, said electronic control system adjusts operation of said prosthetic leg to cause a greater amount of electrical energy generation.

17. The prosthetic leg of claim 15, wherein when said charge status is above some predetermined level, said electronic control system adjusts operation of said prosthetic leg to optimize one or more gait parameters.

18. The prosthetic leg of claim 1, wherein said electronic control system continually monitors the charge status of said at least one electrical energy storage device and correspondingly adjusts operation of said prosthetic leg to best maintain said charge status.

19. The prosthetic leg of claim 1, wherein said electronic control system also distributes electrical energy produced by said actuator/generator to one or more ancillary electrical energy consuming devices associated with said user.

20. The prosthetic leg of claim 19, wherein said ancillary electrical energy consuming devices are selected from the group consisting of other prosthetic limbs, remote sensors, implants, and personal electronic devices.

21. The prosthetic leg of claim 1, wherein said electronic control system controls the transfer of electrical energy from said at least one electrical energy storage device to one or more electrical energy consuming devices.

22. The prosthetic leg of claim 1, wherein said electronic control system operates said prosthetic leg in a gait profile duplication mode.

23. The prosthetic leg of claim 22, wherein data associated with said gait profile is obtained by monitoring and recording the gait of a test subject.

24. The prosthetic leg of claim 22, wherein data associated with said gait profile is calculated based on various characteristics of said user.

25. The prosthetic leg of claim 22, wherein data associated with said gait profile is obtained by instrumenting said user's natural leg and forcing said prosthetic leg to duplicate a time scaled version of a trajectory detected for a previous stride of said natural leg.

26. The prosthetic leg of claim 22, wherein said gait profile is a natural gait profile.

27. The prosthetic leg of claim 22, wherein said electronic control system shifts operation of said prosthetic leg on a sliding scale from said gait profile duplication mode toward a more highly regenerative mode when detected energy consumption exceeds some calculated level.

28. The prosthetic leg of claim 27, wherein actuator/generator gain and/or maximum torque values are limited by said electronic control system when said actuator/generator is expending electrical energy, but remain high when said actuator/generator is generating electrical energy.

29. The prosthetic leg of claim 28, wherein actuator/generator gain and/or maximum torque values during electrical energy generation periods remain high enough to limit heel rise and terminal impact while remaining low enough to allow energy transmitted from said user's hip to said user's shin and foot to overcome frictional forces associated with said knee joint during a swing phase of said user's gait cycle.

30. The prosthetic leg of claim 27, wherein heel rise is scaled to some value between that of the gait profile being duplicated and a smaller angle, thus forcing said user's hip to work harder and causing said actuator/generator to generate a greater amount of electrical energy.

31. The prosthetic leg of claim 30, wherein actuator/generator gain and maximum torque values are kept constant, but heel rise is scaled to some angle between that of a gait profile being duplicated and a gait profile that has a maximum heel rise just larger than necessary to cause a foot portion of said prosthetic leg to clear the floor as a lower portion of said prosthetic leg swings through.

32. The prosthetic leg of claim 1, wherein said electronic control system operates said prosthetic leg in an audible noise minimization mode.

33. The prosthetic leg of claim 32, wherein said knee joint is forced to follow a path of reduced angular travel at near constant speed.

34. The prosthetic leg of claim 33, wherein a degree of knee flexion necessary to allow safe swing through of said prosthetic leg is determined and knee angle is subsequently limited by said electronic control system to some small margin of error above this value.

35. The prosthetic leg of claim 34, further comprising using stride time to determine the time required for said prosthetic leg to reach a point where it will contact the ground and setting knee speed to be as close to constant over the entire stride as possible.

36. The prosthetic leg of claim 32, wherein noise is minimized by constantly maintaining some minimum amount of torque on said actuator/generator.

37. The prosthetic leg of claim 1, wherein the current and/or torque output of said actuator/generator is limited and/or controlled by employing a current controller to control the electric power flowing from said actuator/generator.

38. The prosthetic leg of claim 37, wherein said current controller is a switch mode DC-DC converter that converts said electric power from said actuator/generator into electrical energy at a voltage that can be stored or used concurrently.

39. A prosthetic leg having an active and regenerative knee, comprising:
   a frame;
   a knee joint;
   an auxiliary damping device connected between said frame and said knee joint;
   an actuator/generator in communication with said frame and said knee joint;
   at least one electrical energy storage device in communication with said actuator/generator;
   at least one sensor for monitoring and reporting at least one condition of said prosthetic leg; and
   an electronic control system in communication with said auxiliary damping device, said actuator/generator, said at least one electrical energy storage device, and said at least one sensor;
   wherein said electronic control system operates said actuator/generator in an actuator mode as needed to actively control the gait of said user;
   wherein said auxiliary damping device is used only to supplement said actuator/generator during periods of high torque load on said knee joint;
   wherein bending of said knee joint during ambulation of a user causes a forced actuation of said actuator/generator in a generator mode and the subsequent generation of electrical energy;
   wherein said electronic control system distributes electrical energy to one or more electrical energy consuming devices associated with said prosthetic leg; and
   wherein said electronic control system transfers excess electrical energy produced by said actuator/generator to said at least one electrical energy storage device for later use,
   wherein said electronic control system transfers excess electrical energy produced by said actuator/generator to said at least one electrical energy storage device for later use.

40. The prosthetic leg of claim 39, wherein said auxiliary damping device is selected from the group consisting of hydraulic cylinders, pneumatic cylinders, and magneto-rheological fluid employing devices.

41. The prosthetic leg of claim 39, wherein said actuator/generator is selected from the group consisting of field wound motors, permanent magnet motors, and electroactive polymers.

42. The prosthetic leg of claim 39, wherein said at least one electrical energy storage device is selected from the group consisting of batteries and capacitors.

43. The prosthetic leg of claim 39, wherein said electronic control system controls operation of said prosthetic leg by setting a fixed knee joint flexion torque value based on heel rise, and a fixed knee joint extension torque value based on the time required for said knee joint to reach full extension at some specified amount of time prior to heel contact.

44. The prosthetic leg of claim 39, wherein said electronic control system controls operation of said prosthetic leg by allowing said knee joint to swing freely in flexion until it approaches a specified limit in heel rise angle, at which time said control system causes said actuator/generator to absorb energy from the flexion swing, said control system subsequently allowing said knee to swing back freely until it approaches full extension, at which time energy is absorbed from terminal impact.

45. The prosthetic leg of claim 39, wherein resistance to motion produced by said actuator/generator and/or said auxiliary damping device is proportional to the angular speed of the knee joint, and wherein said electronic control system controls operation of said prosthetic leg by creating flexion and extension settings based on heel rise angle and the timing of terminal impact, respectively.

46. The prosthetic leg of claim 39, wherein said electronic control system controls operation of said prosthetic leg by monitoring the amount of energy produced by rotation of said knee joint and maintaining said amount of energy below some predetermined level based on the position of said knee joint in a heel rise or free swing phase of said user's gait cycle.

47. The prosthetic leg of claim 39, wherein said electronic control system controls operation of said prosthetic leg by modifying said user's gait trajectory in a manner that forces said user to work harder during ambulation, thereby increasing the amount of energy available for recovery and use.

48. The prosthetic leg of claim 47, wherein said electronic control system limits the angle of said knee joint during heel rise.

49. The prosthetic leg of any of claims 43-47, wherein said electronic control system operates said prosthetic leg in a maximized energy regeneration mode.

50. The prosthetic leg of claim 39, wherein said electronic control system operates said prosthetic leg in a maximized energy regeneration mode.

51. The prosthetic leg of claim 39, wherein said electronic control system controls operation of said prosthetic leg by some combination of the methods of claims 43-47.

52. The prosthetic leg of claim 39, wherein said electronic control system controls operation of said prosthetic leg by setting said damping device to limit both heel rise and terminal impact to some predetermined and corresponding range of values, and leaving said setting unchanged unless a change in gait produces a change in heel rise angle or terminal impact timing that falls outside of said range.

53. The prosthetic leg of claim 39, wherein said electronic control system controls operation of said prosthetic leg using a sliding scale that takes into consideration one or more of the current state of charge of said at least one electrical energy storage device, an amount of energy being output by said user, and the type of terrain being traversed.

54. The prosthetic leg of claim 39, wherein said user manually sets said prosthetic leg to operate in a particular manner and said electronic control system simply reports the charge status of said at least one electrical energy storage device.

55. The prosthetic leg of claim 39, wherein said electronic control system continually monitors the charge status of said at least one electrical energy storage device and correspondingly adjusts operation of said prosthetic leg in a manner that results in a greater or lesser amount of electrical energy generation by said actuator/generator.

56. The prosthetic leg of claim 55, wherein when said charge status falls below some predetermined level, said electronic control system adjusts operation of said prosthetic leg to cause a greater amount of electrical energy generation.

57. The prosthetic leg of claim 55, wherein when said charge status is above some predetermined level, said electronic control system adjusts operation of said prosthetic leg to optimize one or more gait parameters.

58. The prosthetic leg of claim 39, wherein said electronic control system continually monitors the charge status of said at least one electrical energy storage device and correspondingly adjusts operation of said prosthetic leg to best maintain said charge status.

59. The prosthetic leg of claim 39, wherein said electronic control system also distributes electrical energy produced by said actuator/generator to one or more other ancillary electrical energy consuming devices associated with said user.

60. The prosthetic leg of claim 59, wherein said ancillary electrical energy consuming devices are selected from the group consisting of other prosthetic limbs, remote sensors, implants, and personal electronic devices.

61. The prosthetic leg of claim 39, wherein said electronic control system operates said prosthetic leg in a gait profile duplication mode.

62. The prosthetic leg of claim 61, wherein data associated with said gait profile is obtained by monitoring and recording the gait of a test subject.

63. The prosthetic leg of claim 61, wherein data associated with said gait profile is calculated based on various characteristics of said user.

64. The prosthetic leg of claim 61, wherein data associated with said gait profile is obtained by instrumenting said user's natural leg and forcing said prosthetic leg to duplicate a time scaled version of a trajectory detected for a previous stride of said natural leg.

65. The prosthetic leg of claim 61, wherein said gait profile is a natural gait profile.

66. The prosthetic leg of claim 61, wherein said electronic control system shifts operation of said prosthetic leg on a sliding scale from said gait profile duplication mode toward a more highly regenerative mode when detected energy consumption exceeds some calculated level.

67. The prosthetic leg of claim 66, wherein actuator/generator gain and/or maximum torque values are limited by said electronic control system when said actuator/generator is expending electrical energy, but remain high when said actuator/generator is generating electrical energy.

68. The prosthetic leg of claim 67, wherein actuator/generator gain and/or maximum torque values during electrical energy generation periods remain high enough to limit heel rise and terminal impact while remaining low enough to allow the energy transmitted from said user's hip to said user's shin and foot to overcome frictional forces associated with said knee joint during a swing phase of said user's gait cycle.

69. The prosthetic leg of claim 68, wherein heel rise is scaled to some angle between that of the gait profile being duplicated and a smaller angle, thus forcing said user's hip to work harder and causing said actuator/generator to generate a greater amount of electrical energy.

70. The prosthetic leg of claim 69, wherein actuator/generator gain and maximum torque values are kept constant, but the angle of heel rise is scaled to some value between that of a gait profile being duplicated and a gait profile that has a maximum heel rise just larger than necessary to cause a foot portion of said prosthetic leg to clear the floor as a lower portion of said prosthetic leg swings through.

71. The prosthetic leg of claim 39, wherein said electronic control system operates said prosthetic leg in an audible noise minimization mode.

72. The prosthetic leg of claim 71, wherein said electronic control system forces said knee joint to follow a path of reduced angular travel at near constant speed.

73. The prosthetic leg of claim 72, wherein a degree of knee flexion necessary to allow safe swing through of said prosthetic leg is determined and knee angle is subsequently limited by said electronic control system to some small margin of error above this value.

74. The prosthetic leg of claim 73, further comprising using stride time to determine the time required for said prosthetic leg to reach a point where it will contact the ground and setting knee speed to be as close to constant over the entire stride as possible.

75. The prosthetic leg of claim 71, wherein noise is minimized by constantly maintaining some minimum amount of torque on said actuator/generator.

76. The prosthetic leg of claim 39, wherein the current and/or torque output of said actuator/generator is limited and/or controlled by employing a current controller to control the electric power flowing from said actuator/generator.

77. The prosthetic leg of claim 76, wherein said current controller is a switch mode DC-DC converter that converts said electric power from said actuator/generator into electrical energy at a voltage that can be stored or used concurrently.

78. A prosthetic leg having an active and regenerative knee, comprising:
 a frame;
 a knee joint;
 a damping device connected between said frame and said knee joint;
 an actuator/generator in communication with said knee joint;
 at least one electrical energy storage device in communication with said actuator/generator;
 at least one sensor for monitoring and reporting at least one condition of said prosthetic leg; and
 an electronic control system in communication with said damping device, said actuator/generator, said at least one electrical energy storage device, and said at least one sensor;
 wherein said damping device is preset to some gross stiffness value and serves as the primary controller of a user's gait;
 wherein said electronic control system operates said actuator/generator in an actuator mode as needed to make adjustments to the gait of said user;
 wherein bending of the knee joint during ambulation of a user causes a forced actuation of said actuator/generator in a generator mode and the subsequent generation of electrical energy;
 wherein said electronic control system distributes electrical energy to one or more electrical energy consuming devices associated with said prosthetic leg; and
 wherein said electronic control system transfers excess electrical energy produced by said actuator/generator to said at least one electrical energy storage device for later use.

79. The prosthetic leg of claim 78, wherein said damping device is selected from the group consisting of hydraulic cylinders, pneumatic cylinders, and magneto-rheological fluid employing brakes or dampers.

80. The prosthetic leg of claim 78, wherein said actuator/generator is selected from the group consisting of field wound motors, permanent magnet motors, and electroactive polymers.

81. The prosthetic leg of claim 78, wherein said at least one electrical energy storage device is selected from the group consisting of batteries and capacitors.

82. The prosthetic leg of claim 78, wherein said electronic control system controls operation of said prosthetic leg by setting a fixed knee joint flexion torque value based on heel rise, and a fixed knee joint extension torque value based on the time required for said knee joint to reach full extension at some specified amount of time prior to heel contact.

83. The prosthetic leg of claim 78, wherein said electronic control system controls operation of said prosthetic leg by allowing said knee joint to swing freely in flexion until it approaches a specified limit in heel rise angle, at which time said control system causes said actuator/generator to absorb energy from the flexion swing, said control system subsequently allowing said knee to swing back freely until it approaches full extension, at which time energy is absorbed from terminal impact.

84. The prosthetic leg of claim 78, wherein resistance to motion produced by said actuator/generator and/or said damping device is proportional to the angular speed of the knee joint, and wherein said electronic control system controls operation of said prosthetic leg by creating flexion and extension settings based on heel rise angle and the timing of terminal impact, respectively.

85. The prosthetic leg of claim 78, wherein said electronic control system controls operation of said prosthetic leg by monitoring the amount of energy produced by rotation of said knee joint and maintaining it below some predetermined level based on the position of said knee joint in a heel rise or free swing phase of said user's gait cycle.

86. The prosthetic leg of claim 78, wherein said electronic control system controls operation of said prosthetic leg by modifying said user's gait trajectory in a manner that forces said user to work harder during ambulation, thereby increasing the amount of energy available for recovery and use.

87. The prosthetic leg of claim 86, wherein said electronic control system limits the angle of said knee joint during heel rise.

88. The prosthetic leg of any of claims 82-86, wherein said electronic control system operates said prosthetic leg in a maximized energy regeneration mode.

89. The prosthetic leg of claim 78, wherein said electronic control system operates said prosthetic leg in a maximized energy regeneration mode.

90. The prosthetic leg of claim 78, wherein said electronic control system controls operation of said prosthetic leg by some combination of the methods of claims 82-86.

91. The prosthetic leg of claim 78, wherein said electronic control system controls operation of said prosthetic leg by setting said damping device to limit both heel rise and terminal impact to some predetermined and corresponding range of values, and leaving said setting unchanged unless a change in gait produces a change in heel rise angle or terminal impact timing that falls outside of said range.

92. The prosthetic leg of claim 78, wherein said electronic control system controls operation of said prosthetic leg using a sliding scale that takes into consideration one or more of the current state of charge of said at least one electrical energy storage device, an amount of energy being output by said user, and the type of terrain being traversed.

93. The prosthetic leg of claim 78, wherein said user manually sets said prosthetic leg to operate in a particular manner and said electronic control system simply reports the charge status of said at least one electrical energy storage device.

94. The prosthetic leg of claim 78, wherein said electronic control system continually monitors the charge status of said at least one electrical energy storage device and correspondingly adjusts operation of said prosthetic leg in a manner that results in a greater or lesser amount of electrical energy generation by said actuator/generator.

95. The prosthetic leg of claim 94, wherein when said charge status falls below some predetermined level, said electronic control system adjusts operation of said prosthetic leg to cause a greater amount of electrical energy generation.

96. The prosthetic leg of claim 94, wherein when said charge status is above some predetermined level, said electronic control system adjusts operation of said prosthetic leg to optimize one or more gait parameters.

97. The prosthetic leg of claim 78, wherein said electronic control system continually monitors the charge status of said at least one electrical energy storage device and correspondingly adjusts operation of said prosthetic leg to best maintain said charge status.

98. The prosthetic leg of claim 78, wherein said electronic control system also distributes electrical energy produced by said actuator/generator to one or more ancillary electrical energy consuming devices associated with said user.

99. The prosthetic leg of claim 98, wherein said ancillary electrical energy consuming devices are selected from the group consisting of other prosthetic limbs, remote sensors, implants, and personal electronic devices.

100. The prosthetic leg of claim 78, wherein said electronic control system operates said prosthetic leg in a gait profile duplication mode.

101. The prosthetic leg of claim 100, wherein data associated with said gait profile is obtained by monitoring and recording the gait of a test subject.

102. The prosthetic leg of claim 100, wherein data associated with said gait profile is calculated based on various characteristics of said user.

103. The prosthetic leg of claim 100, wherein data associated with said gait profile is obtained by instrumenting said user's natural leg and forcing said prosthetic leg to duplicate a time scaled version of a trajectory detected for a previous stride of said natural leg.

104. The prosthetic leg of claim 100, wherein said gait profile is a natural gait profile.

105. The prosthetic leg of claim 100, wherein said electronic control system shifts operation of said prosthetic leg on a sliding scale from said gait profile duplication mode toward a more highly regenerative mode when detected energy consumption exceeds some calculated level.

106. The prosthetic leg of claim 105, wherein actuator/generator gain and/or maximum torque values are limited by said electronic control system when said actuator/generator is expending electrical energy, but remain high when said actuator/generator is generating electrical energy.

107. The prosthetic leg of claim 106, wherein actuator/generator gain and/or maximum torque values during electrical energy generation periods remain high enough to limit heel rise and terminal impact while remaining low enough to allow the energy transmitted from said user's hip to said user's shin and foot to overcome frictional forces associated with said knee joint during a swing phase of said user's gait cycle.

108. The prosthetic leg of claim 105, wherein heel rise is scaled to some angle between that of the gait profile being duplicated and a smaller angle, thus forcing said user's hip to work harder and causing said actuator/generator to generate a greater amount of electrical energy.

109. The prosthetic leg of claim 108, wherein actuator/generator gain and maximum torque values are kept constant, but heel rise is scaled to some angle between that of a gait profile being duplicated and a gait profile that has a maximum heel rise just larger than necessary to cause a foot portion of said prosthetic leg to clear the floor as a lower portion of said prosthetic leg swings through.

110. The prosthetic leg of claim 78, wherein said electronic control system operates said prosthetic leg in an audible noise minimization mode.

111. The prosthetic leg of claim 110, wherein said electronic control system forces said knee joint to follow a path of reduced angular travel at near constant speed.

112. The prosthetic leg of claim 111, wherein a degree of knee flexion necessary to allow safe swing through of said prosthetic leg is determined and knee angle is subsequently limited by said electronic control system to some small margin of error above this value.

113. The prosthetic leg of claim 112, further comprising using stride time to determine the time required for said prosthetic leg to reach a point where it will contact the ground and setting knee speed to be as close to constant over the entire stride as possible.

114. The prosthetic leg of claim 110, wherein noise is minimized by constantly maintaining some minimum amount of torque on said actuator/generator.

115. The prosthetic leg of claim 78, wherein the current and/or torque output of said actuator/generator is limited and/or controlled by employing a current controller to control the electric power flowing from said actuator/generator.

116. The prosthetic leg of claim 115, wherein said current controller is a switch mode DC-DC converter that converts said electric power from said actuator/generator into electrical energy at a voltage that can be stored or used concurrently.

117. A prosthetic leg having an active and regenerative knee, comprising:
a frame;
a knee joint;
an actuator/generator in communication with said frame and said knee joint;
at least one electrical energy storage device in communication with said actuator/generator;
at least one sensor for monitoring and reporting at least one condition of said prosthetic leg; and
an electronic control system in communication with said actuator/generator, said at least one electrical energy storage device, and said at least one sensor;
wherein said electronic control system operates said actuator/generator in an actuator mode as needed to actively control the gait of a user;
wherein bending of said knee joint during ambulation of said user causes a forced actuation of said actuator/generator in a generator mode and the subsequent generation of electrical energy;
wherein said electronic control system distributes electrical energy to one or more electrical energy consuming devices associated with said prosthetic leg; and wherein said electronic control system transfers excess electrical energy produced by said actuator/generator to said at least one electrical energy storage device for later use.

118. The prosthetic leg of claim 117, wherein said actuator/generator is mounted within the knee joint.

119. The prosthetic leg of claim 117, wherein said actuator/generator is selected from the group consisting of permanent magnet motors, field wound motors, and electroactive polymers.

120. The prosthetic leg of claim 117, wherein said at least one electrical energy storage device is selected from the group consisting of batteries and capacitors.

121. The prosthetic leg of claim 117, wherein said electronic control system controls operation of said prosthetic leg by setting a fixed knee joint flexion torque value based on heel rise, and a fixed knee joint extension torque value based on the time required for said knee joint to reach full extension at some specified amount of time prior to heel contact.

122. The prosthetic leg of claim 117, wherein said electronic control system controls operation of said prosthetic leg by allowing said knee joint to swing freely in flexion until it approaches a specified limit in heel rise angle, at which time said control system causes said actuator/generator to absorb energy from the flexion swing, said control system subsequently allowing said knee to swing back freely until it approaches full extension, at which time energy is absorbed from terminal impact.

123. The prosthetic leg of claim 117, wherein resistance to motion produced by said actuator/generator is proportional to the angular speed of said knee joint, and wherein said electronic control system controls operation of said prosthetic leg by creating flexion and extension settings based on heel rise angle and the timing of terminal impact, respectively.

124. The prosthetic leg of claim 117, wherein said electronic control system controls operation of said prosthetic leg by monitoring the amount of energy produced by rotation of said knee joint and maintaining it below some predetermined level based on the position of said knee joint in heel rise or free swing phases of said user's gait cycle.

125. The prosthetic leg of claim 117, wherein said electronic control system controls operation of said prosthetic leg by modifying said user's gait trajectory in a manner that forces said user to work harder during ambulation, thereby increasing the amount of energy available for recovery and use.

126. The prosthetic leg of claim 125, wherein said electronic control system limits the angle of said knee joint during heel rise.

127. The prosthetic leg of any of claims 121-125, wherein said electronic control system operates said prosthetic leg in a maximized energy regeneration mode.

128. The prosthetic leg of claim 117, wherein said electronic control system operates said prosthetic leg in a maximized energy regeneration mode.

129. The prosthetic leg of claim 117, wherein said electronic control system controls operation of said prosthetic leg by some combination of the methods of claims 121-125.

130. The prosthetic leg of claim 117, wherein said electronic control system controls operation of said prosthetic leg using a sliding scale that takes into consideration one or more of the current state of charge of said at least one electrical energy storage device, an amount of energy being output by said user, and the type of terrain being traversed.

131. The prosthetic leg of claim 117, wherein said user manually sets said prosthetic leg to operate in a particular manner and said electronic control system simply reports the charge status of said at least one electrical energy storage device.

132. The prosthetic leg of claim 117, wherein said electronic control system continually monitors the charge status of said at least one electrical energy storage device and correspondingly adjusts operation of said prosthetic leg in a manner that results in a greater or lesser amount of electrical energy generation by said actuator/generator.

133. The prosthetic leg of claim 132, wherein when said charge status falls below some predetermined level, said electronic control system adjusts operation of said prosthetic leg to cause a greater amount of electrical energy generation.

134. The prosthetic leg of claim 132, wherein when said charge status is above some predetermined level, said electronic control system adjusts operation of said prosthetic leg to optimize one or more gait parameters.

135. The prosthetic leg of claim 117, wherein said electronic control system continually monitors the charge status of said at least one electrical energy storage device and correspondingly adjusts operation of said prosthetic leg to best maintain said charge status.

136. The prosthetic leg of claim 117, wherein said electronic control system also distributes electrical energy produced by said actuator/generator to one or more ancillary electrical energy consuming devices associated with said user.

137. The prosthetic leg of claim 136, wherein said ancillary electrical energy consuming devices are selected from the group consisting of other prosthetic limbs, remote sensors, implants, and personal electronic devices.

138. The prosthetic leg of claim 117, wherein said electronic control system operates said prosthetic leg in a gait profile duplication mode.

139. The prosthetic leg of claim 138, wherein data associated with said gait profile is obtained by monitoring and recording the gait of a test subject.

140. The prosthetic leg of claim 138, wherein data associated with said gait profile is calculated based on various characteristics of said user.

141. The prosthetic leg of claim 138, wherein data associated with said gait profile is obtained by instrumenting said user's natural leg and forcing said prosthetic leg to duplicate a time scaled version of a trajectory detected for a previous stride of said natural leg.

142. The prosthetic leg of claim 138, wherein said gait profile is a natural gait profile.

143. The prosthetic leg of claim 138, wherein said electronic control system shifts operation of said prosthetic leg on a sliding scale from said gait profile duplication mode toward a more highly regenerative mode when detected energy consumption exceeds some calculated level.

144. The prosthetic leg of claim 143, wherein actuator/generator gain and/or maximum torque values are limited by said electronic control system when said actuator/generator is expending electrical energy, but remain high when said actuator/generator is generating electrical energy.

145. The prosthetic leg of claim 144, wherein actuator/generator gain and/or maximum torque values during electrical energy generation periods remain high enough to limit heel rise and terminal impact while remaining low enough to allow the energy transmitted from said user's hip to said user's shin and foot to overcome frictional forces associated with said knee joint during a swing phase of said user's gait cycle.

146. The prosthetic leg of claim 138, wherein heel rise is scaled to some angle between that of the gait profile being duplicated and a smaller angle, thus forcing said user's hip to work harder and causing said actuator/generator to generate a greater amount of electrical energy.

147. The prosthetic leg of claim 138, wherein actuator/generator gain and maximum torque values are kept constant, but the trajectory of heel rise is scaled to some angle between that of a gait profile being duplicated and a gait profile that has a maximum heel rise just larger than necessary to cause a foot portion of said prosthetic leg to clear the floor as a lower portion of said prosthetic leg swings through.

148. The prosthetic leg of claim 117, wherein said electronic control system operates said prosthetic leg in an audible noise minimization mode.

149. The prosthetic leg of claim 148, wherein said electronic control system forces said knee joint to follow a path of reduced angular travel at near constant speed.

150. The prosthetic leg of claim 149, wherein a degree of knee flexion necessary to allow safe swing through of said prosthetic leg is determined and knee angle is subsequently limited by said electronic control system to some small margin of error above this value.

151. The prosthetic leg of claim 150, further comprising using stride time to determine the time required for said prosthetic leg to reach a point where it will contact the ground, and setting knee speed to be as close to constant over the entire stride as possible.

152. The prosthetic leg of claim 148, wherein noise is minimized by constantly maintaining some minimum amount of torque on said actuator/generator.

153. The prosthetic leg of claim 117, wherein the current and/or torque output of said actuator/generator is limited and/or controlled by employing a current controller to control the electric power flowing from said actuator/generator.

154. The prosthetic leg of claim 153, wherein said current controller is a switch mode DC-DC converter that converts said electric power from said actuator/generator into electrical energy at a voltage that can be stored or used concurrently.

155. A prosthetic leg having a regenerative knee, comprising:
   a frame;
   a knee joint;
   a damping device connected between said frame and said knee joint, said damping device operative to adjust the gait of a user;
   an actuator/generator associated with said knee joint;
   at least one electrical energy storage device;
   at least one sensor for monitoring and reporting at least one condition of said prosthetic leg; and
   an electronic control system in communication with said damping device, said actuator/generator, said at least one electrical energy storage device, and said at least one sensor;
   wherein said electronic control system adjusts said damping device as needed to regulate the gait of said user;
   wherein bending of the knee joint during ambulation of a user causes a forced movement of said actuator/generator and the subsequent generation of electrical energy;
   wherein said electronic control system concurrently distributes electrical energy produced by said actuator/generator to one or more electrical energy consuming devices associated with said prosthetic leg and/or with said user; and
   wherein additional electrical energy may be drawn from said at least one electrical energy storage device to supplement an amount of electrical energy produced by said actuator/generator.

156. A prosthetic leg having an active and regenerative knee, comprising:
   a frame;
   a knee joint;
   an auxiliary damping device connected between said frame and said knee joint;
   an actuator/generator in communication with said frame and said knee joint;
   at least one electrical energy storage device;
   at least one sensor for monitoring and reporting at least one condition of said prosthetic leg; and
   an electronic control system in communication with said auxiliary damping device, said actuator/generator, said at least one electrical energy storage device, and said at least one sensor;
   wherein said electronic control system operates said actuator/generator in an actuator mode as needed to actively control the gait of said user;
   wherein said auxiliary damping device is used only to supplement said actuator/generator during periods of high torque load on said knee joint;
   wherein bending of said knee joint during ambulation of a user causes a forced actuation of said actuator/generator in a generator mode and the subsequent generation of electrical energy;
   wherein said electronic control system concurrently distributes electrical energy produced by said actuator/generator to one or more electrical energy consuming devices associated with said prosthetic leg and/or with said user; and
   wherein additional electrical energy may be drawn from said at least one electrical energy storage device to supplement an amount of electrical energy produced by said actuator/generator.

157. A prosthetic leg having an active and regenerative knee, comprising:
   a frame;
   a knee joint;
   a damping device connected between said frame and said knee joint;
   an actuator/generator in communication with said knee joint;
   at least one electrical energy storage device;
   at least one sensor for monitoring and reporting at least one condition of said prosthetic leg; and
   an electronic control system in communication with said damping device, said actuator/generator, said at least one electrical energy storage device, and said at least one sensor;
   wherein said damping device is preset to some gross stiffness value and serves as the primary controller of a user's gait;
   wherein said electronic control system operates said actuator/generator in an actuator mode as needed to make adjustments to the gait of said user;
   wherein bending of the knee joint during ambulation of a user causes a forced actuation of said actuator/generator in a generator mode and the subsequent generation of electrical energy;
   wherein said electronic control system concurrently distributes electrical energy produced by said actuator/generator to one or more electrical energy consuming devices associated with said prosthetic leg and/or with said user; and wherein additional electrical energy may be drawn from said at least one electrical energy storage device to supplement an amount of electrical energy produced by said actuator/generator.

158. A prosthetic leg having an active and regenerative knee, comprising:

a frame;

a knee joint;

an actuator/generator in communication with said frame and said knee joint;

at least one electrical energy storage device;

at least one sensor for monitoring and reporting at least one condition of said prosthetic leg; and an electronic control system in communication with said actuator/generator, said at least one electrical energy storage device, and said at least one sensor;

wherein said electronic control system operates said actuator/generator in an actuator mode as needed to actively control the gait of a user;

wherein bending of said knee joint during ambulation of said user causes a forced actuation of said actuator/generator in a generator mode and the subsequent generation of electrical energy;

wherein said electronic control system concurrently distributes electrical energy produced by said actuator/generator to one or more electrical energy consuming devices associated with said prosthetic leg and/or with said user; and wherein additional electrical energy may be drawn from said at least one electrical energy storage device to supplement an amount of electrical energy produced by said actuator/generator.

\* \* \* \* \*